US008906411B2

(12) United States Patent
Bertelsen et al.

(10) Patent No.: US 8,906,411 B2
(45) Date of Patent: Dec. 9, 2014

(54) PRE-COMPACTED CALCIUM-CONTAINING COMPOSITIONS

(75) Inventors: Poul Egon Bertelsen, Roskilde (DK); Peder Mohr Olsen, Kirke Hyllinge (DK)

(73) Assignee: Takeda Nycomed AS, Asker (NO)

( * ) Notice: Subject to any disclaimer, the term of this patent is extended or adjusted under 35 U.S.C. 154(b) by 939 days.

(21) Appl. No.: 12/085,697

(22) PCT Filed: Dec. 7, 2006

(86) PCT No.: PCT/DK2006/000695
§ 371 (c)(1),
(2), (4) Date: May 28, 2008

(87) PCT Pub. No.: WO2007/065440
PCT Pub. Date: Jun. 14, 2007

(65) Prior Publication Data
US 2009/0275540 A1    Nov. 5, 2009

(30) Foreign Application Priority Data
Dec. 7, 2005   (DK) .................................. 2005 01735

(51) Int. Cl.
*A61K 33/06* (2006.01)
*A61K 9/16* (2006.01)
*A61K 31/7004* (2006.01)
*A61K 9/20* (2006.01)
*A23L 1/304* (2006.01)
*A23L 1/09* (2006.01)
*A61K 33/42* (2006.01)
*A23L 1/00* (2006.01)

(52) U.S. Cl.
CPC ........... *A61K 9/1611* (2013.01); *A61K 31/7004* (2013.01); *A61K 9/2009* (2013.01); *A61K 9/2018* (2013.01); *A23L 1/304* (2013.01); *A61K 9/1694* (2013.01); *A23L 1/097* (2013.01); *A61K 33/42* (2013.01); *A61K 33/06* (2013.01); *A61K 9/2095* (2013.01); *A23V 2002/00* (2013.01); *A61K 9/1623* (2013.01); *A23L 1/0017* (2013.01)
USPC ........... 424/465; 424/687; 424/602; 424/464; 424/489

(58) Field of Classification Search
CPC . A61K 9/1694; A61K 9/2018; A61K 9/2095; A61K 33/10; A61K 9/1611; A61K 9/1623; A61K 9/2009; A61K 33/06; A61K 31/7004
See application file for complete search history.

(56) References Cited

U.S. PATENT DOCUMENTS

| | | | |
|---|---|---|---|
| 4,425,332 A * | 1/1984 | James | 424/94.3 |
| 4,830,859 A | 5/1989 | Finnan et al. | |
| 5,108,728 A | 4/1992 | Rau et al. | |
| 6,149,941 A | 11/2000 | Schwarz et al. | |
| 6,475,510 B1 | 11/2002 | Venkatesh et al. | |
| 6,699,845 B2 * | 3/2004 | Oobae et al. | 514/53 |
| 6,740,632 B1 | 5/2004 | Jacob et al. | |
| 7,273,624 B2 * | 9/2007 | Rosenberg et al. | 424/489 |
| 2003/0211168 A1 | 11/2003 | Lynenskjold et al. | |
| 2004/0071772 A1 | 4/2004 | Narita et al. | |
| 2006/0068004 A1* | 3/2006 | Shah | 424/464 |

FOREIGN PATENT DOCUMENTS

| | | |
|---|---|---|
| DE | 20216314 U1 | 12/2003 |
| EP | 0647591 A1 | 4/1995 |
| EP | 0872240 A1 | 10/1998 |
| EP | 0914818 A1 | 5/1999 |
| EP | 0 988 797 | 3/2000 |
| EP | 1126017 A1 | 8/2001 |
| EP | 1369131 A1 | 12/2003 |
| FR | 2 081 364 | 12/1971 |
| JP | 5306229 A | 11/1993 |
| JP | 2001-316249 A | 11/2001 |
| WO | WO-92/10168 A1 | 6/1992 |
| WO | WO-95/08273 A1 | 3/1995 |
| WO | WO-96/09036 A1 | 3/1996 |
| WO | WO-97/41835 A1 | 11/1997 |
| WO | WO-98/52541 | 11/1998 |
| WO | WO-99/06051 | 2/1999 |
| WO | WO-99/65473 | 12/1999 |
| WO | WO-00/28973 | 5/2000 |
| WO | WO-00/76650 A1 | 12/2000 |
| WO | WO-01/83374 A2 | 11/2001 |
| WO | WO-03/055500 A1 | 7/2003 |
| WO | WO-2005/115342 | 12/2005 |

OTHER PUBLICATIONS

Product information sheet for Sturcal L by Specialty Minerals Inc. (1998).*
Bolhuis et al., "DC Calcium lactate, a new filler-binder for direct compaction of tablets", International Journal of Pharmaceuticals, vol. 221, 2001, pp. 77-86.
Bruynseels, et al., "Fluidized-bed process fully established and still developing", Nitrogen No. 183, Jan.-Feb. 1990, pp. 22-26.
CPhI Celebrates ten years of growth in Frankfurt—Manufacturing Chemist, Dec. 31, 1999.
Oneda et al., "The effect of formulation variables on the dissolution and physical properties of spray-dried microspheres containing organic salts", Power Technology, vol. 130, 2003, pp. 377-384.
Rumpler et al., "Continuous Agglomeration and Granulation by Fluidization", Food Marketing & Technology, Apr. 1999, pp. 1-3.

(Continued)

*Primary Examiner* — Bong-Sook Baek
(74) *Attorney, Agent, or Firm* — Edwards Wildman Palmer LLP; Peter F. Corless

(57) ABSTRACT

A pre-compacted materiel comprising one or more calcium-containing compounds and one or more sugar alcohols, wherein the calcium-containing compound having a polycrystallic porous structure. The pre-compacted material is preferably obtained by roller compaction and is suitable for use in the further processing of the pre-compacted material into composition like e.g. tablets.

10 Claims, 23 Drawing Sheets

(56) References Cited

OTHER PUBLICATIONS

"Excipient Systems", http://www.merck.de/english/services/specialchemie/s_chn/pharma/excipients.htm (Nov. 7, 2000).
Merck Formaxx products—marketing information (Sep. 16, 2004).
"2.9.8. Resistance to Crushing of Tablets" European Pharmacopoeia 7.0 p. 267 Jan. 2008:20908.
"2.9.3. Dissolution Test for Solid Dosage Forms" European Pharmacopoeia 7.0 pp. 256-263 Jan. 2010:20903 corrected 6.8.
"2.9.7. Friability of Uncoated Tablets" European Pharmacopoeia 7.0 p. 266 Jan. 2010:20907.
"2.9.1. Disintegration of Tablets and Capsules" European Pharmacopoeia 7.1 pp. 3331-3332 Apr. 2011:20901.
Klobes P et al. "Porosity and Specific Surface Area Measurements for Solid Materials" NIST, (SP 960-17), (2006).

* cited by examiner

PRE-COMPACTED CALCIUM-CONTAINING COMPOSITIONS

FIELD OF THE INVENTION

The present invention relates to a pre-compacted material comprising a polycrystallic and porous calcium-containing compound and a sugar alcohol. SEM photos can be used to identify the structure of the calcium-containing compound with respect to polycrystallic nature and porosity. The invention also relates to a process for the preparation of the pre-compacted material and solid dosage form. The process involves agglomeration of the calcium-containing compound and the pharmaceutically acceptable sugar alcohol by means of roller compaction. The pre-compacted material obtained by roller compaction is suitable for use in the further processing of the pre-compacted material into compositions such as pharmaceutical or nutritional compositions including dosage form like e.g. tablets, capsules, sachets etc. including chewing tablets.

BACKGROUND OF THE INVENTION

Previously it has been described that the quality of the calcium-containing compound as well as the method for preparation of a pharmaceutical composition containing the calcium-containing compound are of great importance in order to obtain acceptable taste and mouth-feel of a chewable tablet (WO 00/28973). In contrast to WO 00/28973 the method according to the invention does not employ a step of binding the particles together by a wet granulation process, which means that the method according to the invention advantageously can be employed when it is desired to incorporate substances that are sensitive towards humidity. An example of such a substance is vitamin D that often is included together with a calcium salt in a pharmaceutically dosage form. The present invention provides a simple and cost-effective alternative method to obtain such a dosage form without the need of a step e.g. involving wet granulation.

To this end, the present inventors have previously found that roller compaction is a suitable method for the preparation of pre-compacted calcium-containing material comprising a regularly shaped calcium-containing compound and a sugar alcohol. However, not all sugar alcohols are equally suitable. Thus, sugar alcohols having a suitable microstructure were favourable to use. An especially suitable quality was sorbitol having a specific small mean particle size of below 50 µm. These findings are described in the co-pending PCT application with application No. PCT/DK2005/000338. U.S. Pat. No. 6,475,510 describes a process for manufacturing bite-dispersion tablets. In Example 6 calcium carbonate is mentioned. However, there is no specification of the quality of calcium carbonate employed and, moreover, a waxy material like e.g. Precirol has been employed. In a material according to the present invention, there is no need to add such a waxy material due to the fact that the quality of the calcium-containing compound is carefully selected. Accordingly, in a specific embodiment, a material according to the present invention does not contain Precirol or any other waxy material as those mentioned in column 5, lines 31-39 of U.S. Pat. No. 6,475,510 (i.e. mono-, di- or tri-C10-C30 aliphatic esters of glycerol, especially glycerol palmito-stearate or glyceryl behenate; the high molecular weight (C10-30) straight chain aliphatic alcohols, such as stearyl alcohol or cetyl alcohol; and mixtures of high molecular weight aliphatic acids and esters; or combinations thereof. Especially, the waxy material is stearyl alcohol or cetyl alcohol, or is glycerol palmito stearate or glyceryl behenate.)

However, there is a need for using roller compaction for other calcium-containing compounds as those of regular shape and, furthermore, there is a need for using other kinds of sugar alcohols as those having binding properties and a micro-structure. Especially, the use of xylitol is of major importance as xylitol has positive impact on the sensoric properties of the end product (e.g. a chewing tablet).

DESCRIPTION OF THE INVENTION

Figure 1:
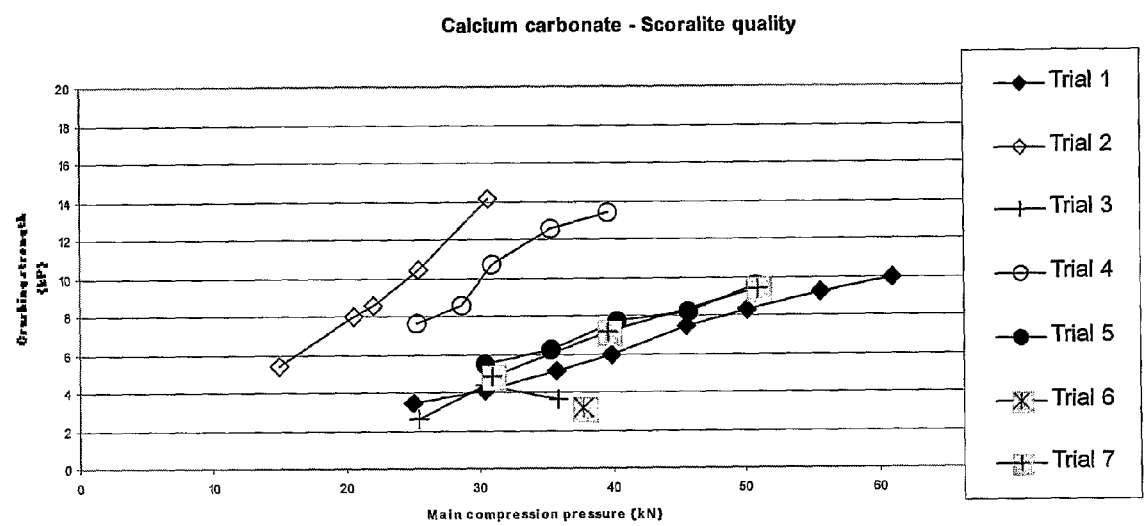
FIG. 1 is a line graph illustrating the crushing strength of tablets based on regularly shaped calcium carbonate (Scoralite quality).

The present invention is based on the finding that it is possible to prepare a pre-compacted calcium-containing material containing a sugar alcohol without any specific requirements to the sugar alcohol provided that the calcium-containing compound itself fulfils specific requirements with respect to crystalline structure and porosity.

More specifically, the present inventors have found that only in those cases where the calcium-containing compound has a polycrystalic and porous structure it is possible to obtain a pre-compacted material that is suitable for use in the manufacturing of dosage forms like tablets.

A polycrystalic structure refers to a material made up of grains of crystalline material where the grains are randomly oriented relative to each other. A polycrystalic structure leads to crystals having an irregular structure, in contrast to e.g. cubes with smooth surfaces (regular shape crystals). This irregular structure is herein also referred to as a porous structure.

In the present context, the term "pre-compacted" is intended to denote the initial compaction of materials ("having a particle size below approx. 100 µm") aiming at achieving a flowable granulate, which later in the manufacturing process may be further compacted into tablets.

As mentioned above, in the present context the process of roller compacting of a powder is applied as an alternative method to known granulation or agglomeration methods, i.e. wet granulation or—when tablets are prepared—direct compression using dry binders. The present inventors have previously found that the process of roller compacting is a very mild method that does not destroy the possibility of obtaining products that have an acceptable mouth-feel and at the same time are without a dominating chalk-like taste or feel. However, the finding was limited to regularly shaped calcium-containing compounds and sugar alcohols with binding properties and of a microporous structure.

Normally, roller compaction is employed with the purpose of increasing the bulk density of a particular substance or composition e.g. in order to transform a bulky material to a less voluminous material that is easier to use in the manufacturing of pharmaceutical compositions. However, roller compaction is normally not used as a gentle granulation process that maintains or do not destroy important properties of the material (i.e. the calcium-containing compound) so that an acceptable taste, mouthfeel etc. can be obtained.

With an aim of preparing a smaller tablet that still has acceptable taste and mouthfeel, the present inventors have found that the use pharmaceutically acceptable sugar alcohols in the agglomeration process is particularly suitable. However, in order to obtain suitable properties of a roller compacted composition containing a calcium-containing compound, the present inventors have previously found that two major factors are important, namely the properties of the calcium-containing compound itself and the choice of sugar alcohol used as a binder in the agglomeration process, as discussed above. However, the present invention eliminates this restriction with respect to choice of sugar alcohols provided that the calcium-containing compound has a polycrystallic and porous structure.

Accordingly, in one aspect the invention relates to a pre-compacted materiel comprising one or more calcium-containing compounds and one or more sugar alcohols, the calcium-containing compound having a polycrystallic porous structure.

As demonstrated in the examples herein (see Example 3) it is not sufficient for the calcium-containing compound to have a non-regular shape in order to enable the preparation of a suitable pre-compacted material. Example 3 demonstrates that Dicafos PA, which is a non-regularly shaped calcium-containing compound (see FIG. 6), does not have sufficient properties in order to enable being successfully roller compacted with a sugar alcohol. Accordingly, the porous character of the calcium-containing compound is of importance.

Normally, the concentration of the calcium-containing compound in a pre-compacted material according to the invention is about 60% w/w or more such as, e.g., about 65% w/w or more, about 70% w/w or more, about 75% w/w or more, about 80% w/w or more, about 85% w/w or more, about 90% w/w or more or about 95% w/w or more.

In contrast to what was expected by the inventors, experiments performed by the inventors have shown that calcium-containing compounds in qualities that are applicable for direct compression not automatically serve as a good starting point for roller compaction. From Example 3 and 6 herein it is seen that a DC quality must also be porous in order to enable preparation of suitable pre-compacted material and subsequently further processing thereof into e.g. tablets.

As described above, it is especially advantageous to pre-compact the calcium-containing compound together with one or more sugar alcohols. From the examples herein it is seen that a relatively broad concentration range can be employed without changing the over-all properties of the pre-compacted material with respect to tabletting. Moreover, when the calcium-containing compound has the required polycrystallic and porous nature, the examples herein show that the structure (e.g. crystalline, micro-structure, porosity etc.) of the sugar alcohol has minor impact on the resulting product with respect to technical properties.

Suitable sugar alcohols for use in a pre-compacted material according to the invention include xylitol, sorbitol, mannitol, maltitol, lactitol, erythritol, inositol, isomalt, and mixtures thereof.

With respect to the concentration of the one or more sugar alcohols in a pre-compacted material according to the invention it is normally about 5% w/w or more such as, e.g., about 7.5% or more, about 10% w/w or more, about 15% w/w or more, about 20% w/w or more, about 25% w/w or more, about 30% w/w or more, about 35% w/w or more or about 40% w/w.

As mentioned above, the most important properties are the polycrystallic and porous nature of the calcium-containing compound. These properties can be seen in SEM photos, cf. the examples herein. Provided that these properties are present, the calcium-containing compound may be selected from the group consisting of calcium carbonate, calcium citrate, calcium lactate, calcium phosphate including tricalcium phosphate, calcium gluconate, bisglycino calcium, calcium citrate maleate, hydroxyapatite including solvates thereof, and mixtures thereof.

As it appears from the examples herein, specifically suitable calcium-containing compounds are calcium carbonate and calcium phosphates.

Accordingly, in one embodiment, the calcium-containing compound is calcium carbonate such as, e.g, Sturcal including e.g. Sturcal L. In another embodiment the calcium-containing compound is a calcium phosphate including a tri-calcium phosphate, a di-calcium phosphate or a mono-calcium phosphate. Suitable qualities include tricalcium phosphate ($Ca_5(PO_4)_3OH$) and dicalcium phosphate ($CaHPO_4$).

In another embodiment, the calcium-containing compound is in a direct compressible form.

Specific embodiments of the invention include pre-compacted material comprising Sturcal L and xylitol; Sturcal L and mannitol; Sturcal L and maltitol; Tricafos P and xylitol; Tricafos P and mannitol; Tricafos P and maltitol; Tricafos A and xylitol; Tricafos A and mannitol; Tricafos A and maltitol.

Sturcal may also be of D, H, LS, M or X qualities or mixtures thereof, and Tricafos may be of S or R qualities or mixtures thereof. Moreover Dicafos may be of AN quality.

In a still further embodiment, a pre-compacted material according to the invention further comprises a sugar alcohol different from xylitol, mannitol or maltitol.

In such cases, the total concentration of the one or more sugar alcohols in the final composition is from about 5% w/w to about 40% w/w such as, e.g., about 5% w/w, about 10% w/w, about 25% w/w or about 40%.

Use of roller compaction as a means for agglomeration of a calcium-containing compounds to obtain a pre-compacted material that is suitable for use in the preparation of e.g. chewable tablets having an acceptable taste and mouth-feel, has two critical parameters with respect to the calcium-containing compound, namely the polycrystallinity and the porosity.

In a paragraph given in the following, a description of calcium-containing compounds is given. However, as mentioned herein before, the calcium-containing compound for use in the roller compaction process according to the invention is polycrystalline and porous such as a calcium salt like calcium carbonate in specific qualities. In preferred aspect, the calcium salt is calcium carbonate and notably with a shape and a mean particle size corresponding to that of Sturcal L, or a calcium phosphate like e.g. Dicafos A or Tricafos P.

However, the above-mentioned calcium-containing compound may be used in admixture with other calcium-containing compounds such as, e.g., those mentioned herein in the following paragraph, especially calcium citrate, calcium lactate, calcium phosphate including tricalcium phosphate, calcium gluconate, bisglycino calcium, calcium citrate maleate, hydroxyapatite including solvates, and mixtures thereof.

In a specific aspect, a pre-compacted material according to the invention contains the above-mentioned polycrystallic and porous calcium-containing compound and another calcium-containing compound (i.e. irrespective of its crystalline nature and porous structure). In a specific embodiment, a pre-compacted material according to the invention further comprises a calcium-containing compound that has a non-porous structure. In such cases, the weight ratio between the non-porous calcium-containing compound and the polycrystallic porous calcium-containing compound is normally at the most 0.4 such as, e.g., at the most 0.35, at the most 0.3, at the most 0.25, at the most 0.2, at the most 0.15, at the most 0.1 or at the most 0.05.

More specifically, the polycrystallic porous calcium-containing compound may be Sturcal L, Tricafos P or Dicafos A or mixtures thereof and the non-porous calcium-containing compound may be Scoralite or Cafos DB or mixtures thereof.

In those cases, where calcium-containing compounds of different structures and natures are present, the concentration of the non-porous calcium-containing compound is normally from about 5% to about 40% such as, e.g., at 40% w/w or less, 25% w/w or less, 10% w/w or less or 5% w/w or less.

Normally, the content of the polycrystallic and porous calcium-containing compound in the pre-compacted material is in a range of from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w or at least about 75% w/w.

The pre-compacted material obtained by roller compaction may comprise 100% w/w of the calcium-containing compound or it may comprise from about 50% to about 90% w/w such as, e.g., from about 70 to about 80% w/w of the total amount of calcium-containing compound contained in the tablet. Accordingly, a part of the total amount of calcium-containing compound may be added after roller compaction.

A pre-compacted material according to the invention may further comprise one or more pharmaceutically acceptable excipients or additives, or one or more therapeutically, prophylactically and/or diagnostically active substances. A description of pharmaceutically acceptable excipients suitable for use in the present context is given herein.

A particular active substance of interest is a vitamin D.

In another aspect, the invention relates to the use of a pre-compacted material as described herein for the preparation of a composition including a pharmaceutical or nutritional composition. In a specific embodiment the invention relates to a solid dosage form comprising the pre-compacted material according to the invention.

A dosage form according to the invention comprises a pre-compacted material optionally together with one or more pharmaceutically acceptable excipients.

Specific embodiments of interest are those wherein the dosage form of the invention is in the form of tablets (including chewing tablets, suckable tablets and swallowable tablets), capsules, sachets or the like.

In general, the concentration of the polycrystallic porous calcium-containing compound in a composition of the invention (such as in a tablet) is 50% w/w or more such as, e.g., about 55% w/w or more, about 60% w/w or more, about 65% w/w or more, about 70% w/w or more, about 75% w/w or more, about 80% w/w or more, about 85% w/w or more or about 90% w/w or more.

Furthermore, roller compaction of a composition containing a calcium-containing compound and a sugar alcohol to obtain a pre-compacted material according to the invention leads to a pre-compacted material that has such a flowability that—when tablets are prepared from the pre-compacted material optionally admixed with at the most 10% w/w such as, e.g. at the most about 7.5% w/w or at the most about 5% w/w of a glidant using a tabletting machine operating at least 300 tablets per min—the mass variation of the tablets obtained fulfils the requirements given in Ph. Eur. The tabletting machine may be operating at e.g. 1000 tablets/min or even higher such as, e.g., 2000 tablets/min, 3000 tablets/min, 4000 tablets/min, 5000 tablets/min, 6500 tablets/min, 700 tablets/min or 8000 tablets/min etc. The dwell time during the preparation of the tablets is at the most about 1 sec.

In a specific embodiment a pre-compacted material according to the invention contains from about 60 to about 95% w/w of the calcium-containing compound and from about 5 to about 40% w/w of the pharmaceutically acceptable sugar alcohol, provided that the sum does not exceed 100% w/w.

In another specific embodiment a pre-compacted material according to the invention contains from about 60 to about 94% w/w such as, e.g., from about 65% to about 80% w/w of the calcium-containing compound, from about 5 to about 35% w/w such as, e.g., from about 15 to about 30% w/w of the pharmaceutically acceptable sugar alcohol and from about 1 to about 15% w/w of one or more pharmaceutically acceptable excipients and/or active substances, provided that the sum of ingredients amounts to 100% w/w.

More specifically, a pre-compacted material according to the invention preferably contains from about 65% to about 80% w/w such as, e.g., from about 70% to about 75% w/w of the calcium-containing compound and from about 15% to about 25% w/w such as, e.g., from about 20 to about 25% w/w of sorbitol or isomalt or mixtures thereof.

A pre-compacted material according to the invention may be used as such, but normally it is manufactured into a suitable solid dosage form. One or more pharmaceutically acceptable excipients may be added in order to prepare the dosage form. The dosage form is intended for oral administration e.g. in the form of a single unit or a multiple unit dosage form such as, e.g., in the form of tablets, capsules, sachets, beads, pellets or the like.

In a preferred embodiment, the solid dosage form according to the invention is in the form of tablets.

A solid dosage form according to the invention may contain an amount of the one or more calcium-containing compounds corresponding to from about 300 to about 1200 mg calcium such as, e.g., from about 400 to about 600 mg calcium. Normally, the total concentration of the one or more calcium-containing compound in the dosage form is in a range of from about 40% to about 99% w/w such as, e.g., from about 45% to about 98% w/w, from about 50% to about 95% w/w, from about 55% to about 90% w/w or at least about 60% w/w, at least about 65% w/w, at least about 70% w/w.

In a specific embodiment, the total concentration of the pre-compacted material contained in the dosage form is from about 65% to about 100% w/w such as, e.g., from about 70% to about 98% w/w, from about 75% to about 95% w/w, from about 80% to about 95% or from about 85% to about 95% w/w.

In another specific embodiment, a solid dosage form according to the invention contains from about 60% to about 95% w/w of the calcium-containing compound and from about 5% to about 40% w/w of the pharmaceutically acceptable sugar alcohol, provided that the sum does not exceed 100% w/w. Alternatively, a solid dosage form contains from about 60 to about 94% w/w such as, e.g., from about 65% to about 80% w/w of the calcium-containing compound, from about 5 to about 35% w/w such as, e.g., from about 15 to about 30% w/w of the pharmaceutically acceptable sugar alcohol and from about 1 to about 15% w/w of one or more pharmaceutically acceptable excipients and/or active substances, provided that the sum of ingredients amounts to 100% w/w.

A SEM photo of a fractured surface of the solid dosage form shows that a surface of a deformed particle of sugar alcohol is in close contact with surfaces of the one or more calcium-containing compound.

In a preferred aspect, a solid dosage form is in the form of a chewable, suckable and/or swallowable tablet. Importantly for chewable tablets is the taste and such tablets of the invention must have an acceptable taste with respect to sweetness, flavour and chalkiness when tested by a professional/skilled sensory test panel of at least 6 persons.

A solid dosage form according to the invention may comprise a sweetener selected from the group consisting of dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt (e.g. calcium cyclamate, sodium cyclamate), neohesperidine dihydrochalcone, thaumatin, saccharin, saccharin salt (e.g. ammonium saccharin, calcium saccharin, potassium saccharin, sodium saccharin), and mixtures thereof.

The invention also relates to a process for the preparation of a pre-compacted material as defined above, the process comprises roller compaction of a composition comprising the polycrystallic and porous calcium-containing compound and one or more pharmaceutically acceptable sugar alcohols. Details concerning the main aspect of the invention (i.e. the pre-compacted material) apply mutatis mutandis to this and other aspects of the invention.

A further aspect of the invention is to combine the manufacture of a pre-compacted material and the manufacture of tablets. By use of pocket rollers on the roller compactor a powder mixture can be transformed directly into a solid dosage form, that is a tablet.

A further aspect of the invention is a process for preparing a tablet comprising a calcium-containing compound, the process comprises
i) preparing a pre-compacted material as defined herein,
ii) optionally admixing one or more pharmaceutically acceptable excipients or additive and/or one or more active substances, and
iii) compressing the material into tablets.

Normally, the compression in step iii) is performed at a compression force that is adjusted with respect to the diameter and the desired height of the tablet so that the compression force applied is at the most about 80 kN such as, e.g., at the most 70 kN, at the most 60 kN, at the most 50 kN, at the most about 40 kN, at the most about 30 kN or at the most about 20 kN when tablets having a diameter of about 16 mm or is capsule shaped (9.4×18.9 mm) and a resulting height of at the most about 10 mm such as, e.g., about 9 mm, about 8 mm or about 7 mm, about 6 mm or about 5 mm are obtained.

Specifically, the invention relates to a process according for the preparation of a tablet comprising i)
calcium carbonate, calcium phosphate or mixtures thereof
ii) sorbitol and/or isomalt (in other embodiments maltitol and/or xylitol may be included),
iii) a vitamin D, and
iv) optionally one or more pharmaceutically acceptable excipients.

The tablet may comprise
i) from about 50% to about 95% w/w of calcium carbonate,
ii) from about 5 to about 40% w/w of sorbitol and/or isomalt,
iii) from about 0.01 to about 1% w/w of a vitamin D, and
iv) optionally one or more pharmaceutically acceptable excipients
with the proviso that the total amount of ingredients corresponds to about 100% w/w.

Calcium-Containing Compound

The calcium-containing compound contained in a pre-compacted material made according to the invention is a physiologically tolerable calcium-containing compound that is therapeutically and/or prophylactically active.

Calcium is essential for a number of key functions in the body, both as ionized calcium and a calcium complex (Campell A K. Clin Sci 1987; 72:1-10). Cell behaviour and growth are regulated by calcium. In association with troponin, calcium controls muscle contraction and relaxation (Ebashi S. Proc R Soc Lond 1980; 207:259-86).

Calcium selected channels are a universal feature of the cell membrane and the electrical activity of nerve tissue and the discharge of neurosecretory granules are a function of the balance between intracellular and extra cellular calcium levels (Burgoyne R D. Biochim Biophys Acta 1984; 779:201-16). The secretion of hormones and the activity of key enzymes and proteins are dependent on calcium. Finally calcium as a calcium phosphate complex confers rigidity and strength on the skeleton (Boskey A L. Springer, 1988: 171-26). Because bone contains over 99% of the total body calcium, skeletal calcium also serves as the major long-term calcium reservoir.

Calcium salts such as, e.g., calcium carbonate or calcium phosphate is used as a source of calcium especially for patients suffering from or at risk of osteoporosis. Moreover, calcium carbonate is used as an acid-neutralizing agent in antacid tablets.

As mentioned above, calcium has a number of important functions within the mammalian body in particular in humans. Furthermore, in many animal models, chronic low calcium intake produces osteopenia. The osteopenia affects cancellous bone more than cortical bone and may not be completely reversible with calcium supplementation. If the animal is growing reduced calcium intake leads to stunting. In the premature human neonate the higher the calcium intake, the greater the increase in skeletal calcium accretion which, if high enough, can equal gestational calcium retention. During growth chronic calcium deficiency causes rickets. Calcium supplements in both pre- and postpubertal healthy children leads to increased bone mass. In adolescents the higher the calcium intake, the greater the calcium retention, with the highest retention occurring just after menarche. Taken together, these data suggest that in children and adolescents considered to be taking an adequate intake of calcium, peak bone mass can be optimized by supplementing the diet with calcium. The mechanisms involved in optimizing deposition of calcium in the skeleton during growth are unknown. They are probably innate properties of the mineralization process that ensures optimal calcification of the osteoid if calcium supplies are high. The factors responsible for stunting of growth in states of calcium deficiency are also unknown but clearly involve growth factors regulating skeletal size.

In adults calcium supplementation reduces the rate of age-related bone loss (Dawson-Hughes B. Am J Clin Nut 1991; 54:S274-80). Calcium supplements are important for individuals who cannot or will nor achieve optimal calcium intakes from food. Furthermore, calcium supplement is important in the prevention and treatment of osteoporosis etc.

Furthermore, calcium may have anticancer actions within the colon. Several preliminary studies have shown high calcium diets or intake of calcium supplementation is associated with reduced colon rectal cancer. There is increasing evidence that calcium in combination with acetylsalicylic acid (ASA) and other non-steroidal anti-inflammatory drugs (NSAIDS) reduce the risk the risk of colorectal cancer.

Recent research studies suggest that calcium might relieve premenstrual syndrome (PMS). Some researchers believe that disruptions in calcium regulation are an underlying factor in the development of PMS symptoms. In one study, half the women of a 466 person group of pre-menopausal women from across the U.S. were tracked for three menstrual cycles and were given 1200 mg of calcium supplements daily throughout the cycle. The final results showed that 48% of the women who took placebo had PMS related symptoms. Only 30% of those receiving calcium tablets did.

Calcium salts like e.g. calcium carbonate is used in tablets and due to the high dose of calcium required, such tablets are often in the form of chewable tablets. It is a challenge to formulate e.g. chewable tablets containing a calcium salt, which tablets have a pleasant taste and an acceptable mouth feel without the characteristic dominating taste or feeling of chalk.

A calcium-containing compound for use according to the invention may be e.g. bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Other calcium sources may be water-soluble calcium salts, or complexes like e.g. calcium alginate, calcium-EDTA and the like or organic compounds containing calcium like e.g. calcium organophosphates. Use of bone meal, dolomite and other unrefined calcium sources is discouraged because these sources may contain lead and other toxic contaminants. However, such sources may be relevant if they are purified to a desired degree.

The calcium-containing compound may be used alone or in combination with other calcium-containing compounds.

Of specific interest is bisglycino calcium, calcium acetate, calcium carbonate, calcium chloride, calcium citrate, calcium citrate malate, calcium cornate, calcium fluoride, calcium glubionate, calcium gluconate, calcium glycerophosphate, calcium hydrogen phosphate, calcium hydroxyapatite, calcium lactate, calcium lactobionate, calcium lactogluconate, calcium phosphate, calcium pidolate, calcium stearate and tricalcium phosphate. Mixtures of different calcium-containing compounds may also be used. As appears from the examples herein, calcium carbonate and calcium phosphates are especially suitable for use as a calcium-containing compound and calcium carbonate, tricalcium phosphate ($Ca_5(PO_4)OH$) and β-tricalcium phosphate ($Ca_3(PO_4)$) have a high content of calcium, whereas dicalcium phosphate ($CaHPO_4$) has a lower content of calcium but is available in high density qualities.

Of particular interest is calcium carbonate and calcium phosphate.

Normally, a tablet made according to the invention contains an amount of the calcium-containing compound corresponding to from about 100 to about 1000 mg Ca such as, e.g., from about 150 to about 800 mg, from about 200 to about 700 mg, from about 200 to about 600 mg or from about 200 to about 500 mg Ca.

Calcium carbonate Calcium carbonate can be in three different crystal structures: calcite, aragonite and vaterite. Mineralogically, these are specific mineral phases, which relate to the distinct arrangement of the calcium, carbon and oxygen atoms in the crystal structure. These distinct phases influence the shape and symmetry of the crystal forms. For example, calcite is available in four different shapes: scalenohedral, prismatic, spherical and rhombohedral, and aragonit crystals can be obtained as e.g. discrete or clustered needle-like shapes. Other shapes are also available such as, e.g., cubic shapes (Scoralite 1A+B from Scora).

As shown in the examples herein, a particular suitable quality of calcium carbonate is calcium carbonate having a mean particle size of 60 μm or less such as, e.g., 50 μm or less or 40 μm or less.

Furthermore, an interesting quality of calcium carbonate has a bulk density below 2 g/mL.

Calcium carbonate 2064 Merck (available from Merck, Darmstadt, Germany) that has a mean particle size of 10-30 μm, an apparent bulk density of 0.4 to 0.7 g/mL, and a specific surface area of 0.3 m$^2$/g;

Calcium carbonate 2069 Merck (available from Merck, Darmstadt, Germany) that has a mean particle size of approx. 3.9 μm, and an apparent bulk density of 0.4 to 0.7 g/mL;

Scoralite 1A (available from Scora Watrigant SA, France) has a mean particle size of 5 to 20 μm, an apparent bulk density of 0.7 to 1.0 g/mL, and a specific surface area of 0.6 m$^2$/g;

Scoralite 1B (available from Scora Watrigant SA, France) has a mean particle size of 10-25 μm, an apparent bulk density of 0.9 to 1.2 g/mL, and a specific surface area of 0.4 to 0.6 m$^2$/g;

Scoralite 1A+B (available from Scora Watrigant SA, France) have a mean particle size of 7-25 μm, an apparent bulk density of 0.7 to 1.2 g/mL, and a specific surface area of 0.35 to 0.8 m$^2$/g;

Pharmacarb LL (available from Chr. Hansen, Mahawah N.J.) L has a mean particle size of 12-16 μm, an apparent bulk density of 1.0 to 1.5 g/mL, and a specific surface area of 0.7 m$^2$/g;

Sturcal H (available from Specialty Minerals, Bethlehem, Pa.) has a mean particle size of approx. 4 μm, an apparent bulk density of 0.48 to 0.61 g/mL;

Sturcal F (available from Specialty Minerals, Bethlehem, Pa.) has a mean particle size of approx. 2.5 μm, an apparent bulk density of 0.32 to 0.43 g/mL;

Sturcal M (available from Specialty Minerals, Bethlehem, Pa.) has a mean particle size of 7 μm, an apparent bulk density of 0.7 to 1.0 g/mL, and a specific surface area of 1.5 m$^2$/g;

Sturcal L (available from Specialty Minerals, Bethlehem, Pa.) has a mean particle size of approx. 7 μm, an apparent bulk density of 0.78 to 0.96 g/mL, Sturcal L consists of scalenohedral shaped crystals;

Socal P2PHV (available from Solvay, Brussels, Belgium) has a mean particle size of 1.5 μm, an apparent bulk density of 0.28 g/mL, and a specific surface area of 7.0 m$^2$/g Socal P2PHV consists of scalenohedral shaped crystals;

Mikhart 10, SPL, 15, 40 and 65 (available from Provencale, Provencale, France);

Mikhart 10 has a mean particle size of 10 μm,
Mikhart SPL has a mean particle size of 20 μm,
Mikhart 15 has a mean particle size of 17 μm,
Mikhart 40 has a mean particle size of 30 μm, an apparent bulk density of 1.1 to 1.5 g/mL;
Mikhart 65 has a mean particle size of 60 μm, an apparent bulk density of 1.25 to 1.7 g/mL;

Hubercal Elite 500 (available from J.M. Huber Corp., USA) has a mean particle size of 5.8 μm and a specific surface area of 1.8 m$^2$/g;

Hubercal Elite 500 (available from J.M. Huber Corp., USA) has a mean particle size of 8.2 μm and a specific surface area of 1.3 m$^2$/g.

Omyapure 35, (available from Omya S.A.S, Paris, France) has a mean particle size of 5-30 μm, and a specific surface area of 2.9 m$^2$/g;

Calci Pure 250 Heavy, Calci Pure 250 Extra Heavy and Calci Pure GCC HD 212 with a mean particle size of 10-30 μm, an apparent bulk density of 0.9-1.2 g/ml, and a specific surface area of 0.7 m$^2$/g (available from Particle Dynamic Inc., St. Louis Mont.).

Calcium Phosphate

DI-CAFOS A (CaHPO$_4$) (available from Chemische Fabrik Buddenheim KG, Buddenheim, Germany) that has a mean particle size of approximately 70 μm and a bulk density of approximately 1.3 g/ml and a polycrystallic and porous nature;

DI-CAFOS PA (CaHPO$_4$) (available from Chemische Fabrik Buddenheim KG, Buddenheim, Germany) that has a mean particle size <7 μm and a bulk density of approximately 0.9 g/ml TRI-CAFOS S (Ca$_5$(PO$_4$)$_3$OH (available from Chemische Fabrik Buddenheim KG, Buddenheim, Germany) that has a mean particle size <6 μm and a bulk density of approximately 0.25 g/ml and a polycrystallic and porous nature;

TRI-CAFOS S (Ca$_5$(PO$_4$)$_3$OH (available from Chemische Fabrik Buddenheim KG, Buddenheim, Germany) that has a mean particle size of approximately 70 μm and a bulk density of approximately 0.5 g/ml;

CAFOS DB (Ca$_3$(PO$_4$)$_2$ (available from Chemische Fabrik Buddenheim KG, Buddenheim, Germany) that has a mean particle size <5 μm and a bulk density of approximately 0.6 g/ml;

Other qualities may also be suitable for use according to the invention provided that they are of a polycrystallic nature and porous.

The content of the calcium-containing compound in a tablet made according to the present invention is in a range from about 40% to about 100% w/w such as, e.g., from about 45% to about 98% w/w, from about 50% to about 95% w/w, from about 55% to about 90% w/w or at least about 60% w/w, at least about 65% w/w, at least about 70% w/w or at least about 75% w/w.

Normally, the dose of calcium for therapeutic or prophylactic purposes is from about 350 mg (e.g. newborn) to about 1200 mg (lactating women) daily. The amount of the calcium-containing compound in the tablets can be adjusted to that the tablets are suitable for administration 1-4 times daily, preferably once or twice daily.

As mentioned above, the granulate obtained by the method according to the invention may be used as such, but it is also very suitable for further manufacturing into solid dosage forms like e.g. tablets, capsules or sachets.

A person skilled in the art will know how to adjust the composition and the various process parameters in order to obtain a desired calcium-containing product.

In one embodiment of the invention, the granulate obtained by the present method is intended to be manufactured into tablets. Often it is necessary to add one or more pharmaceutically acceptable excipients (e.g. lubricants) in order to avoid adherence and/or increase flowability of the granulate obtained. Accordingly, the method may also comprise a step of mixing the granulate obtained with one or more pharmaceutically acceptable excipients.

In the event that it is desired to include other active substances than the calcium-containing compound, the method may also comprise a step of adding one or more therapeutically, prophylactically and/or diagnostically active substance to the granulate obtained.

Such substances include one or more nutrients such as, e.g., one or more vitamins or minerals. In a specific embodiment, the further active substance is a D-vitamin such as, e.g., $D_3$ vitamin, $D_2$ vitamin or derivatives thereof.

D Vitamin or Other Active Substances

A pre-compacted material as well as a tablet obtained according to the invention may comprise a further therapeutically and/or prophylactically active substance. Of particular interest are one or more D-vitamin compounds. Non-limiting examples are dry vitamin D3, 100 CWS available from Roche and dry vitamin D3 100 GFP available from BASF.

A pre-compacted material or tablet made according to the invention may comprise a further therapeutically and/or prophylactically active substance, or it may contain one or more nutrients such as, e.g. one or more vitamins or minerals. Of specific interest are e.g. vitamin B, vitamin C, vitamin D and/or vitamin K and minerals like e.g. zink, magnesium, selenium etc.

Of particular interest are one or more D-vitamin compounds such as, e.g., Vitamin $D_2$ (ergocalciferol) and Vitamin $D_3$ (cholecalciferol) including dry vitamin $D_3$, 100 CWS available from Roche and dry vitamin $D_3$ 100 GFP available from BASF.

In addition to its action on calcium and skeletal homeostasis, vitamin D is involved in the regulation of several major systems in the body. The actions of vitamin D are medicated at the genome by a complex formed by 1,25-$(OH)_2$ vitamin D mainly produced in the kidney, with the vitamin D receptor (VDR). The latter is widely distributed in many cell types. The 1,25-$(OH)_2$ vitamin D/VDR complex has important regulatory roles in cell differentiation and in the immune system. Some of these actions are probably dependant on the ability of certain tissues other than the kidney to produce 1,25-$(OH)_2$ vitamin D locally and act as a paracrine (Adams J S et al. Endocrinology 1996; 137:4514-7).

In humans, deficiency of vitamin D results in rickets in children and osteomalacia in adults. The basic abnormality is a delay in the rate of mineralization off osteoid as it is laid down by the osteoblast (Peacock M. London Livingstone, 1993:83-118). It is not clear whether this delay is due to a failure of a 1,25-$(OH)_2$ vitamin D-dependant mechanism in the osteoblast or to reduced supplies of calcium and phosphate secondary to malabsorption or a combination of both. Accompanying the mineralization delay, there is reduced supply of calcium and phosphate, severe secondary hyperparathyroidism with hypocalcaemia and hypophosphatemia and increased bone turnover.

Vitamin D insufficiency, the preclinical phase of vitamin D deficiency, also causes a reduced calcium supply and secondary hyperparathyroidism, albeit of a milder degree than found with deficiency. If this state remains chronic, osteopenia results. The biochemical process underlying this state of calcium insufficiency is probably inappropriate level of 1,25-$(OH)_2$ vitamin D due to a reduction in its substrate 25-OHD (Francis R M et al. Eur J Clin Invest 1983; 13:391-6). The state of vitamin D insufficiency is most commonly found in the elderly. With age there is a decrease in serum 25-OH vitamin D due to decreased sunlight exposure and possible to decreased skin synthesis. Furthermore, in the elderly the condition is exacerbated by a decrease in calcium intake and a paradoxical decrease in calcium absorption. The reduction in renal function with age giving rise to reduced renal 1,25-$(OH)_2$ vitamin D production may be a contributing factor. There are a number of studies of the effects of vitamin D supplementation on bone loss in the elderly. Some are without calcium supplementation and others are with calcium supplementation. It appears from the studies that although vitamin D supplementation is necessary to reverse deficiency and insufficiency, it is even more important as far as the skeleton is concerned to provide calcium supplementation since the major skeletal defect is calcium deficiency. In literature based on clinical trials, recent findings suggest trends of need for higher doses of vitamin D for the elderly patients (Compston J E. BMJ 1998; 317:1466-67). An open quasi-randomised study of annual injections of 150.000-300.000 IU of vitamin D (corresponding to approx. 400-800 IU/day) showed a significant reduction in overall fracture rate but not in the rate of hip fracture in treated patients (Heikinheimo R J et al. Calcif Tissue Int 1992; 51:105-110).

As it appears from above, a combination of calcium and vitamin D is of interest. The recommended Daily Allowance (RDA) of calcium and vitamin $D_3$ are as follows (European Commission. Report on osteoporosis in the European Community. Action for prevention. Office for official Publications of the European Communities, Luxembourg 1998):

| Group | Age (years) | Calcium (mg)* | Vitamin $D_3$ (µg) |
|---|---|---|---|
| Newborn | 0-0.5 | 400 | 10-25 |
|  | 0.5-1.0 | 360-400 | 10-25 |
| Children | 1.0-3.0 | 400-600 | 10 |
|  | 4.0-7.0 | 450-600 | 0-10 |
|  | 8.0-10 | 550-700 | 0-10 |
| Men | 11-17 | 900-1000 | 0-10 |
|  | 18-24 | 900-1000 | 0-15 |
|  | 25-65 | 700-800 | 0-10 |
|  | 65+ | 700-800 | 10 |
| Women | 11-17 | 900-1000 | 0-15 |
|  | 18-24 | 900-1000 | 0-10 |
|  | 25-50 | 700-800 | 0-10 |
|  | 51-65 | 800 | 0-10 |
|  | 65+ | 700-800 | 10 |
| Pregnant |  | 700-900 | 10 |
| Lactating |  | 1200 | 10 |

*RDA of calcium varies from country to country and is being re-evaluated in many countries.

Vitamin D is very sensitive towards humidity and is subject to degradation. Therefore, vitamin D is often administered in a protective matrix. Accordingly, when tablets are prepared containing a vitamin D it is of utmost importance that the compression forces applied during the tabletting step do not decrease the protective effect of the matrix and thereby impair the stability of vitamin D. To this end, the combination of the various ingredients in a granulate or tablet made according to the invention has proved to be very suitable in those cases where vitamin D also is incorporated into the composition as it is possible to employ a relatively low compression force during tabletting and still achieve a tablet with suitable mechanical strength (crushing strength, friability etc.).

In a specific embodiment, the invention provides a tablet comprising
i) a calcium-containing compound as an active substance,
ii) a vitamin D, and
iii) optionally one or more pharmaceutically acceptable excipients or actives.

More specifically, the tablet may comprise
i) at least 200 mg of the calcium-containing compound (normal range 200-1500 mg),
ii) at least 5 µg of vitamin D (normal range 5-100 µg–1 µg=40 IU), and
iii) optionally one or more pharmaceutically acceptable excipients or actives.

In a specific embodiment, the invention provides a tablet comprising
i) from about 50% to about 90% w/w of the calcium-containing compound,
ii) from about 0.00029% o about 0.0122% w/w of a vitamin D, and
iii) optionally one or more pharmaceutically acceptable excipients or actives
with the proviso that the total amount of ingredients corresponds to about 100% w/w.

In particular, the tablet may comprise
i) from about 50% to about 90% w/w of the calcium-containing compound,
ii) from about 5 to about 40% w/w of a sweetening agent,
iii) from about 0.12% to about 4.9% w/w of a vitamin D including a protective matrix,
iv) optionally one or more pharmaceutically acceptable excipients or actives
with the proviso that the total amount of ingredients corresponds to about 100% w/w.

Pharmaceutically Acceptable Excipients

In the present context, the term "pharmaceutically acceptable excipient" is intended to denote any material, which is inert in the sense that it substantially does not have any therapeutic and/or prophylactic effect per se. A pharmaceutically acceptable excipient may be added to the active drug substance with the purpose of making it possible to obtain a pharmaceutical composition, which has acceptable technical properties. Although a pharmaceutically acceptable excipient may have some influence on the release of the active drug substance, materials useful for obtaining modified release are not included in this definition.

The calcium-containing compound and the sugar alcohol may also be admixed with one or more pharmaceutically acceptable excipients before or after roller compaction. Such excipients include those normally used in formulation of solid dosage forms such as, e.g. fillers, binders, disintegrants, lubricants, flavouring agents, colouring agents, including sweeteners, pH adjusting agents, stabilizing agents, etc.

Typically, a disintegrant is selected from the group consisting of: croscarmellose sodium (a cross-linked polymer of carboxymethylcellulose sodium), crospovidone, starch NF; polacrilin sodium or potassium and sodium starch glycolate. Those skilled in the art will appreciate that it is desirable for compressible tablets to disintegrate within 30 minutes, more desirable within 10 min, most desirable within 5 min; therefore, the disintegrant used preferably results in the disintegration of the tablet within 30 minutes, more preferable within 10 min, most preferable within 5 min.

Examples of disintegrants that may be used are e.g. cellulose derivatives, including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®).

Fillers/diluents/binders may be incorporated such as polyols, sucrose, sorbitol, mannitol, Erythritol®, Tagatose®, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium sulfate, calcium carbonate.

In pharmaceutical compositions made according to the present invention, especially microcrystalline cellulose, L-hydroxypropylcellulose, dextrins, maltodextrins, starches and modified starches may be well suited.

In a specific embodiment of the invention, the calcium-containing compound may be roller compacted together with one or more pharmaceutically acceptable binders, or a binder may be added after roller compaction. Suitable binders include those normally used within the pharmaceutical field although binders usually employed in wet granulation processes are not likely to be able to function to the same extent as essentially no liquid is present in during the agglomeration.

More specifically, examples include
cellulose derivates including methylcellulose, hydroxypropylcellulose (HPC, L-HPC), hydroxypropylmethylcellulose (HPMC), microcrystalline cellulose (MCC), sodium carboxymethylcellulose (Na-CMC), etc.;
mono- di-, oligo-, polysaccharides including dextrose, fructose, glucose, isomalt, lactose, maltose, sucrose, tagatose, trehalose, inulin and maltodextrin;
polyols including sugar alcohols such as, e.g, lactitol, maltitol, mannitol, sorbitol, xylitol and inositol;
polyvinylpyrrolidone including Kollidon K30, Kollidon 90F or Kollidon VA64 and
proteins including casein.

Glidants and lubricants may be incorporated such as stearic acid, metallic stearates, talc, waxes and glycerides with high melting temperatures, colloidal silica, sodium stearyl fumarate, polyethyleneglycols and alkyl sulphates.

Surfactants may be employed such as non-ionic (e.g., polysorbate 20, polysorbate 21, polysorbate 40, polysorbate 60, polysorbate 61, polysorbate 65, polysorbate 80, polysorbate 81, polysorbate 85, polysorbate 120, sorbitane monoisostearate, sorbitanmonolaurate, sorbitan monopalmitate, sorbitan monostearate, sorbitan monooleate, sorbitan sesquioleate, sorbitan trioleate, glyceryl monooleate and polyvinylalkohol), anionic (e.g., docusate sodium and sodium lauryl sulphate) and cationic (e.g., benzalkonium chloride, benzethonium chloride and cetrimide) or mixtures thereof.

Other appropriate pharmaceutically acceptable excipients may include colorants, flavouring agents, and buffering agents.

As appears from the claims, the present invention also provides a method comprising the step of processing the pre-compacted material obtained by roller compaction into a solid dosage form. Such dosage forms may be provided with a coating provided that the coating does not substantially retard the release of the active drug substance from the composition. Typically, a film coating may be employed.

Suitable lubricants include talc, magnesium stearate, calcium stearate, stearic acid, hydrogenated vegetable oils and the like. Preferably, magnesium stearate is used.

Suitable bulking agents include xylitol, mannitol, compressible sugars, lactose, calcium phosphate and microcrystalline celluloses.

Suitable artificial sweeteners include dextrose, fructose, glycerin, glucose, isomalt, lactitol, lactose, maltitol, maltose, mannitol, sorbitol, sucrose, tagatose, trehalose, xylitol, alitame, aspartame, acesulfam potassium, cyclamic acid, cyclamate salt (e.g. calcium cyclamate, sodium cyclamate), neohesperidine dihydrochalcone, thaumatin, saccharin, saccharin salt (e.g. ammonium saccharin, calcium saccharin, potassium saccharin, sodium saccharin), and mixtures thereof.

If desired known flavourants and known FD & C colorants can be added to the composition.

Example 1

Comparison of Tablets Based on Roller Compaction of Regularly Shaped and Polycrystalline and Porous Calcium Carbonate Compounds The investigations were based on the following formulation:

TABLE 1

Formulation based on regularly shaped calcium carbonate.

| Raw materials | Trial 1 | Trial 2 | Trial 3 | Trial 4 | Trial 5 | Trial 6 | Trial 7 |
|---|---|---|---|---|---|---|---|
| Calcium carbonate Scoralite | 75.96 | 75.96 | 75.96 | 75.96 | 75.96 | 75.96 | 75.96 |
| Sorbitol D(v; 0.5) 110 μm | 23.70 | | | | | | |
| Sorbitol D(v; 0.5) 38 μm | | 23.70 | | | | | |
| Xylitol D(v; 0.5) 34 μm | | | 23.70 | | | | |
| Isomalt D(v; 0.5) 27.5 μm | | | | 23.70 | | | |
| Isomalt D(v; 0.5) 136.5 μm | | | | | 23.70 | | |
| Mannitol D(v; 0.5) 48.2 μm | | | | | | 23.70 | |
| Maltitol D(v; 0.5) 31 μm | | | | | | | 23.70 |
| Magnesium stearate | 0.34 | 0.34 | 0.34 | 0.34 | 0.34 | 0.34 | 0.34 |

TABLE 2

Formulation based on polycrystalline and porous calcium carbonate.

| Raw materials | Trial 8 | Trial 9 | Trial 10 | Trial 11 | Trial 12 | Trial 13 | Trial 14 |
|---|---|---|---|---|---|---|---|
| Calcium carbonate Sturcal L | 75.96 | 75.96 | 75.96 | 75.96 | 75.96 | 75.96 | 75.96 |
| Sorbitol D(v; 0.5) 110 μm | 23.70 | | | | | | |
| Sorbitol D(v; 0.5) 38 μm | | 23.70 | | | | | |
| Xylitol D(v; 0.5) 34 μm | | | 23.70 | | | | |
| Isomalt D(v; 0.5) 27.5 μm | | | | 23.70 | | | |
| Isomalt D(v; 0.5) 136.5 μm | | | | | 23.70 | | |
| Mannitol D(v; 0.5) 48.2 μm | | | | | | 23.70 | |
| Maltitol D(v; 0.5) 31 μm | | | | | | | 23.70 |
| Magnesium stearate | 0.34 | 0.34 | 0.34 | 0.34 | 0.34 | 0.34 | 0.34 |

For all trials from 1-14 the sugar alcohols were lump breaked in an oscillating sieve using a 250 μm screen and afterwards mixed with calcium carbonate in a high-shear mixer (Fielder PM 25 at low impeller speed and no chopper) for 2 minutes.

The mixtures were granulated on a roller compactor (Gerteis 3W-Polygran). Finally, lubrication with magnesium stearate was done manually.

The roller compaction was based on a setup with knurled rollers and control. The key set up parameters are: Gap Width (GW), Force (F), Roller Speed (RS) and screen size.

TABLE 3

Roller compactor parameters.

| | |
|---|---|
| GW, mm | 3.5 |
| F, kN/cm | 12 |
| RS, rpm | 5 |
| Screen size, mm | 1.5 |

The granulates were tabletted on a Fette PT1090 fully instrumented tablet press with oval shaped (18.9×9.4 mm) punches. Tablet weight was approximately 1,683 mg. All in-process crushing strength data are obtained using a Schleuniger AT4.

Figure 2:
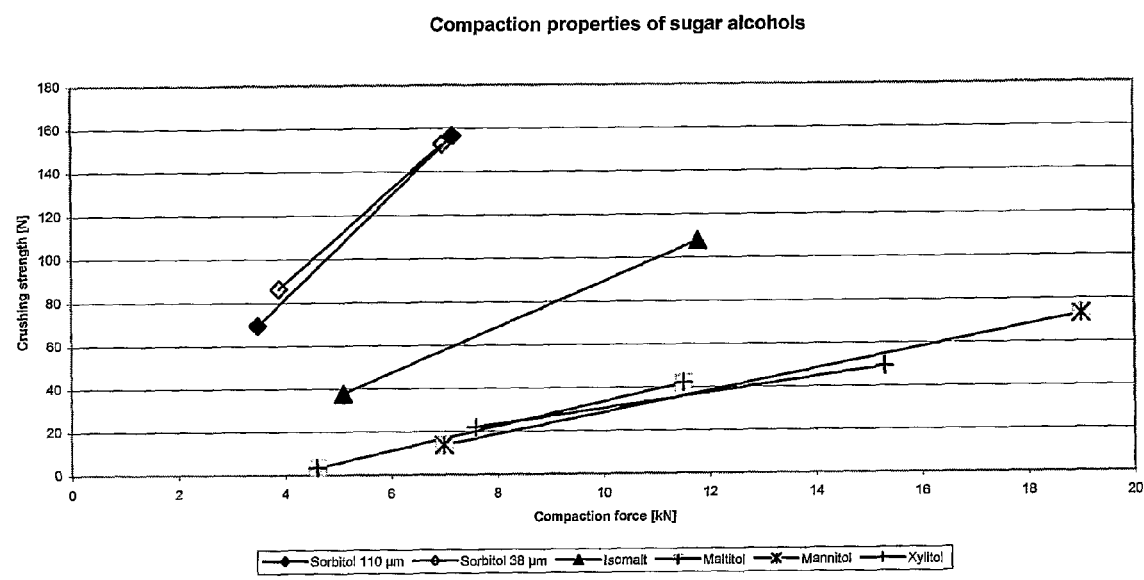
FIG. 2 is a line graph demonstrating the crushing strength of tablets based solely on individual sugar alcohols.
Figure 3:
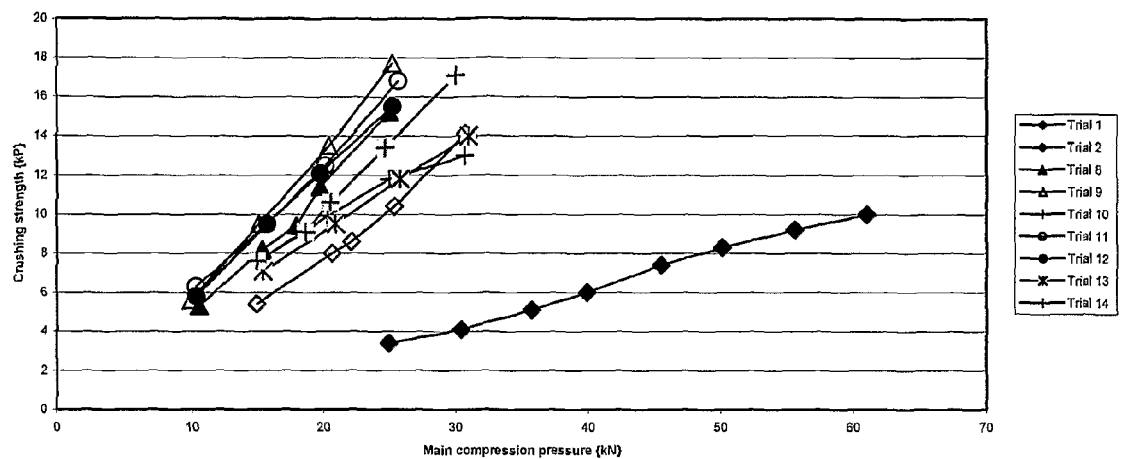
FIG. 3 is a line graph showing the crushing strength of tablet based on non-regularly shaped calcium carbonate (Sturcal L quality) compared to crushing strength of tablets based on regularly shaped calcium carbonate (Scoralite quality).

Based on FIG. 1 it can be seen that for regularly shaped calcium carbonate the type and particle size of the chosen sugar alcohol has a significant impact on the crushing strength. Sorbitol or isomalt having a fine particle size are preferable. The impact on tablet crushing strength of the different sugar alcohols can be explained by a difference in compaction properties as shown in FIG. 2. In this figure the crushing strengths of tablets based solely on the individual sugar alcohol have been measured. However, based on FIG. 3, it can be seen that for non-regularly shaped calcium carbonate the type and particle size of the sugar alcohol becomes of no importance for practical use. All tablets containing non-regularly shaped calcium carbonate have crushing strengths at or above the maximum of what can be obtained by using regularly shaped calcium carbonate in combination with the preferred sugar alcohols having a fine particle size.

Figure 4:
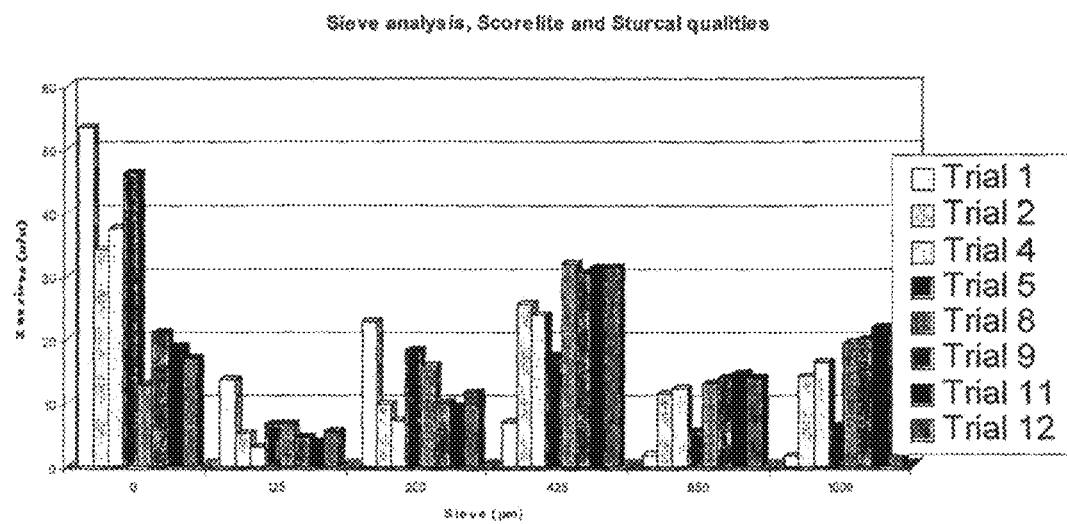
FIG. 4 is a bar chart illustrating Sieve analysis of granulates containing regularly shaped calcium carbonate (Scoralite quality) and granulates containing non-regularly shaped calcium carbonate (Sturcal L quality).

The better compaction properties of polycrystalline and porous calcium-containing compounds observed when comparing crushing strengths of tablets based on regularly shaped and polycrystalline and porous calcium carbonate can also be found when comparing sieve analysis of the matching granulates as shown in FIG. 4. In this figure a significantly higher amount of fines, that is particles below 125 μm, can be seen in batches containing the regularly shaped calcium carbonate. The higher amount of fines is caused by less optimal compaction properties

Example 2

Comparison of Tablets with Different Content of Sugar Alcohol Based on Roller Compaction of Polycrystalline and Porous Calcium Carbonate Compounds The investigations were based on the following formulation. Trial numbers

|  | Xylitol amount (% w/w) | | | | Xylitol/Sorbitol amount (% w/w) |
| --- | --- | --- | --- | --- | --- |
|  | 5 | 10 | 25 | 40 | 30/10 |
| Calcium carbonate Sturcal L, trial No. | 40 | 41 | 42 | 43 | 44 |

For all trials the sugar alcohols were lump breaked in an oscillating sieve using a 250 μm screen and afterwards manually mixed with calcium carbonate.

For all trials the mixtures were granulated on a roller compactor according to example 1.

For all trials lubrication with magnesium stearate (0.3%) was done manually.

The granulates were tabletted on a Fette PT1090 fully instrumented tablet press with oval shaped (18.9×9.4 mm) punches. Tablet weight was adjusted to achieve a tablet height of 7.0±0.1 mm. All in-process crushing strength data were obtained using a Schleuniger AT4.

Figure 10:
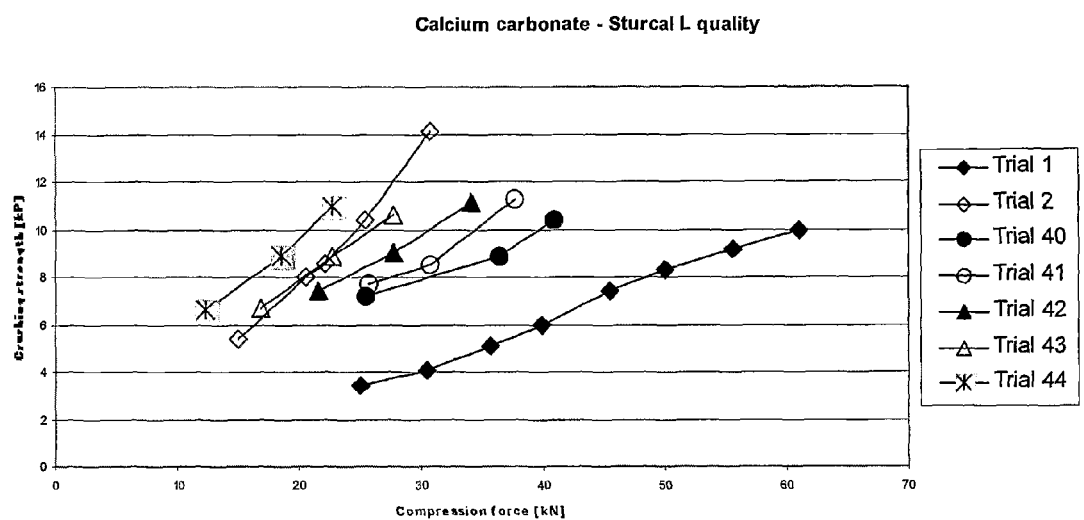
FIG. 10 is a line graph showing the crushing strength of tablet based on non-regularly shaped calcium carbonate (Sturcal L quality) compared to crushing strength of tablets based on regularly shaped calcium carbonate (Scoralite quality).

From FIG. 10 can be seen that, as expected from example 1, use of a concentration of xylitol around 25% gives compaction properties as seen when using regularly shaped calcium carbonate and the sorbitol with the optimal particle size, i.e. of a smaller size than that of "instant sorbitol".

Concentrations of xylitol at 5 and 10% lead to somewhat less optimal compaction properties as evidenced by the necessity of using a higher compression force to obtain suitable crushing strengths. This means that the use of a calcium carbonate having a polycrystallic porous structure allows the addition of xylitol in amounts high enough to have an impact on the sensoric properties of the tablets. The addition of xylitol is needed as the sensoric properties of Sturcal L are markedly poorer that what can be experienced when using Scoralite.

A further discussion of compaction properties is continued in example 6.

Example 3

Comparison of Tablets Based on Roller Compaction of Calcium Phosphate Containing Compounds The addition of xylitol is needed as the sensoric properties of tablets containing calcium phosphate are markedly poorer compared to tablets containing Scoralite. In this context it would be a clear advantage if variations in the concentration of xylitol could be done with limited or no impact on tablet crushing strength. This means that the full impact of the taste masking properties of the xylitol can be exploited. This is a challenge as xylitol is a sugar alcohol with poor compaction properties as seen from example 1, FIG. 2.

The investigations were based on the following formulation:

TABLE 1

| Formulation based on calcium phosphate. Trial numbers | | | | | |
| --- | --- | --- | --- | --- | --- |
|  | Xylitol amount (% w/w) | | | | Xylitol/Sorbitol amount (% w/w) |
|  | 5 | 10 | 25 | 40 | 30/10 |
| Tri-Cafos P, Trial No. [tricalcium phosphate] $Ca_5(PO_4)_3OH$ Psd 6 μm *, Trial No. | 15 | 16 | 17 | 18 | 19 |
| Di-Cafos PA [dicalcium phosphate] $CaHPO_4$, Psd: 7 μm, Trial No. | 20 | 21 | 22 | 23 | 24 |
| Cafos DB [β-tricalcium phosphate] $Ca_3(PO_4)_2$ Psd: 5 μm, Trial No. | 25 | 26 | 27 | 28 | 29 |
| Tri-Cafos S [tricalcium phosphate] $Ca_5(PO_4)_3OH$ Psd: DC **, Trial No. | 30 | 31 | 32 | 33 | 34 |
| Di-Cafos A [dicalcium phosphate] $CaHPO_4$ Psd: DC**, Trial No. | 35 | 36 | 37 | 38 | 39 |

* Psd: mean particle size based on D(v; 0.5)
** DC: direct compressible

For all trials the sugar alcohols were lump breaked in an oscillating sieve using a 250 μm screen and afterwards manually mixed with calcium phosphate.

For trials from 15-29 the mixtures were granulated on a roller compactor according to example 1.

For trials from 30-39 no granulation of the mixtures were necessary in order to achieve a granulate ready for tabletting as the calcium compounds were of a DC-quality.

For all trials lubrication with magnesium stearate (0.3%) was done manually.

The granulates were tabletted on a Fette PT1090 fully instrumented tablet press with oval shaped (18.9×9.4 mm) punches. Tablet weight was adjusted to achieve a tablet height of 7.0±0.1 mm. All in-process crushing strength data were obtained using a Schleuniger AT4.

Figure 5:
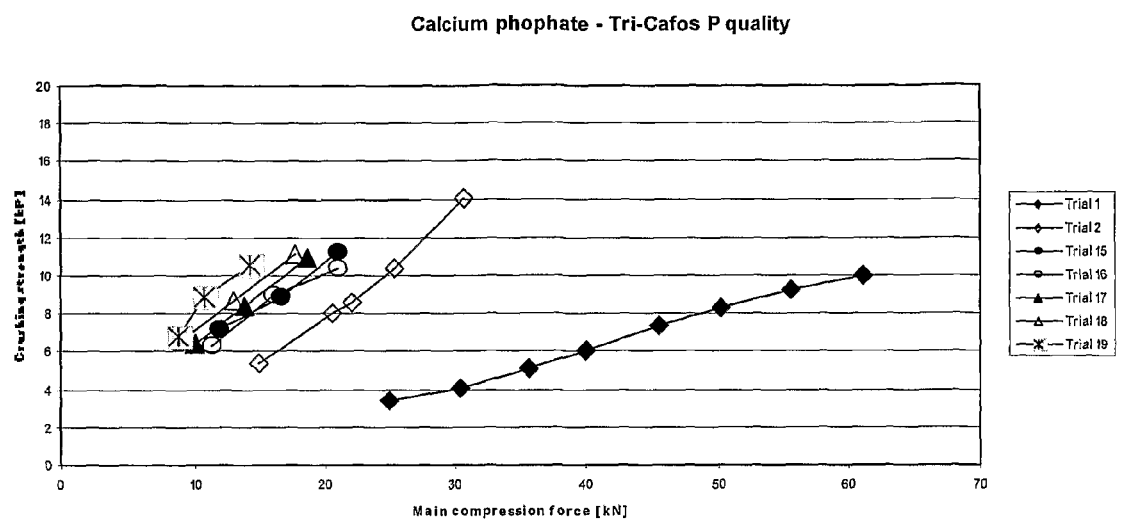
FIG. 5 is a line graph showing the crushing strength of tablets based on non-regularly shaped calcium phosphate (Tri-Cafos P quality) compared to crushing strength of tablets based on regularly shaped calcium carbonate (Scoralite quality).

Based on FIG. 5 it can be seen that the use of a tricalcium phosphate in a Tri-Cafos P quality requires a lower main compression force in order to achieve the same crushing strength as when using regularly shaped calcium carbonate and the sorbitol with the optimal particle size (trial 2). This is achieved even though the calcium phosphate is diluted by a sugar alcohol having poor compaction properties (see example 1, FIG. 2). Furthermore, no significant impact on crushing strength of the xylitol concentration is seen.

Figure 6:
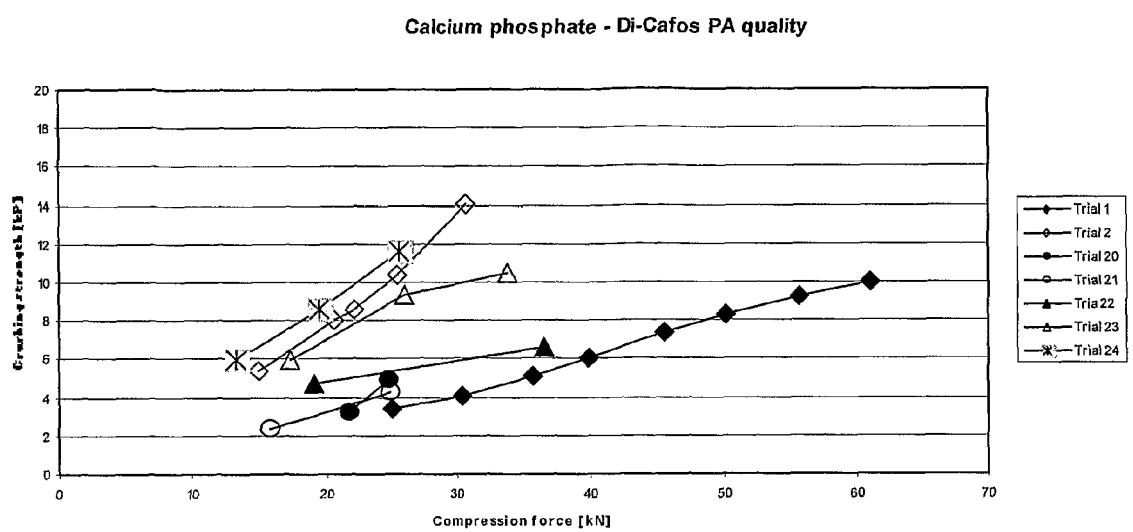
FIG. 6 is a line graph demonstrating the crushing strength of tablets based on non-regularly shaped phosphate (Di-Cafos PA quality) compared to crushing strength of tablets based on regularly shaped calcium carbonate (Scoralite quality).

From FIG. 6 it can be seen that in order to achieve tablets having a crushing strength comparable to trial 2 approximately the double amount of sugar alcohol is needed when the calcium compound is Dicafos PA. This is caused by both the poor compaction properties of xylitol as shown in FIG. 2 and that xylitol is not subdivided during compression as is the case for sorbitol.

Figure 22:
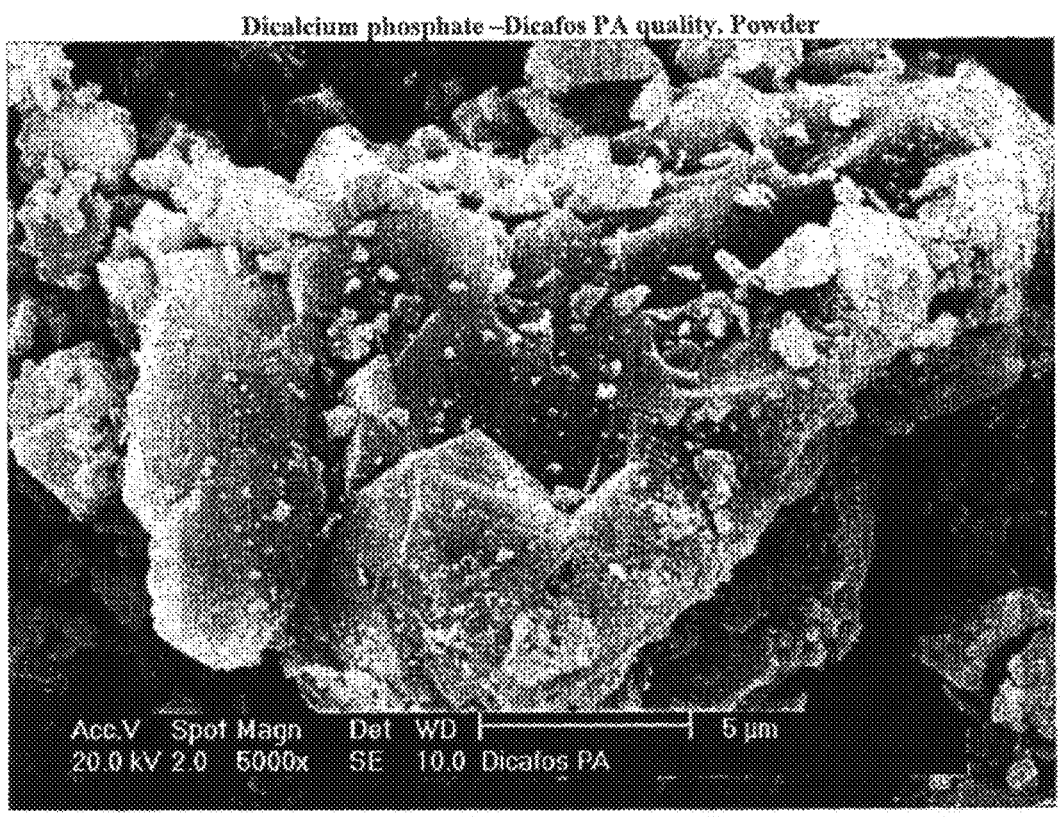
FIG. 22 is a photomicrograph illustrating SEM-Analysis of tablets based on non-regularly shaped calcium phosphate (Di-Cafos PA quality).

Moreover, the Dicafos PA employed in FIG. 6 is a non-regularly shaped calcium-containing compound (see FIG. 22). Accordingly, non-regularity of the calcium-containing compound does not suffice in order to enable roller compaction of a calcium-containing compound and a sugar alcohol. As described herein it is important that the calcium-containing compound has a polycrystallic and porous nature. From FIG. 6 it is seen that Dicafos PA is compact in itself, i.e. it does not have a porous structure. Furthermore Dicafos PA is not polycrystalline.

When comparing FIGS. 6 and 5 it can be seen that Dicafos PA has poorer compaction properties than Tricafos P. This is further illustrated in example 6.

Figure 7:
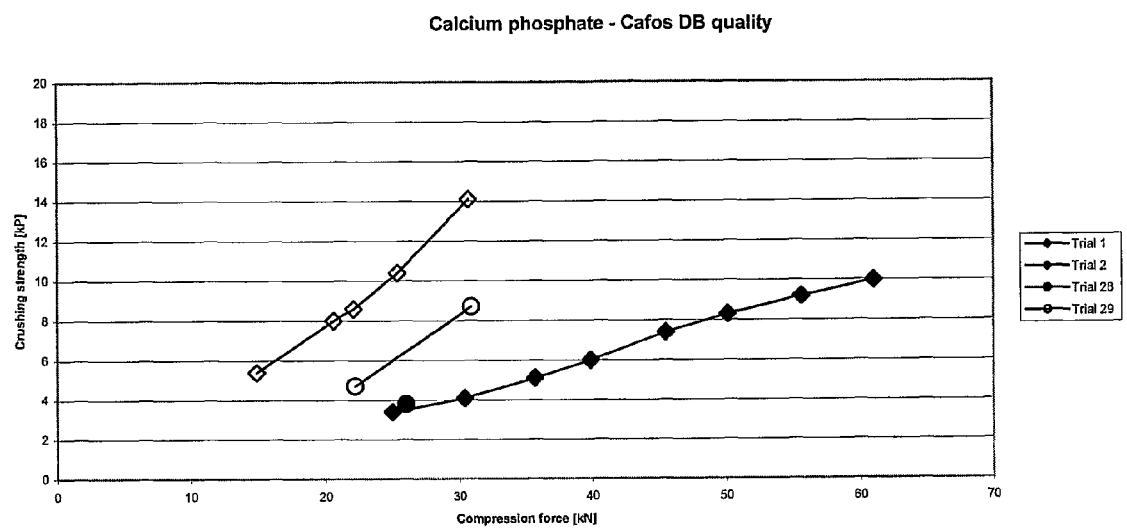
FIG. 7 is a line graph illustrating the crushing strength of tablets based on non-porous tricalcium phosphate (Cafos DB quality) compared to crushing strength of tablets based on regularly shaped calcium carbonate (Scoralite quality).

From FIG. 7 can be seen that the use of β-tricalcium phosphate in a Cafos DB quality results in a granulate with poor compaction properties. As a consequence of this it was not possible from trial 25-27 to obtain satisfactory tablets and tablets from trial 28-29 were capping. This matter is further discussed in example 6.

Figure 8:
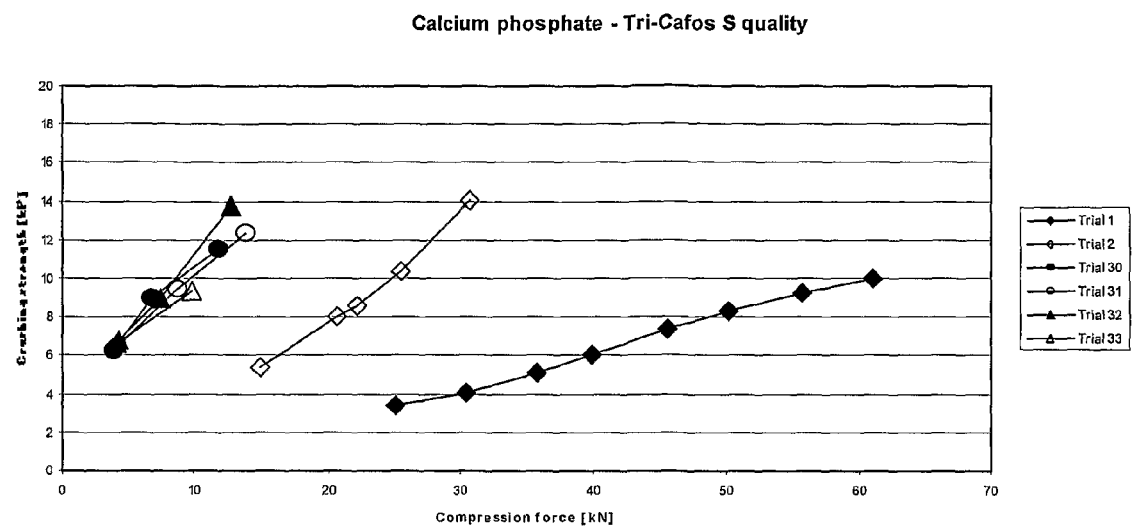
FIG. 8 is a line graph showing the crushing strength of tablets based on non-porous tricalcium phosphate (Tri-Cafos S quality) compared to crushing strength of tablets based on regularly shaped calcium carbonate (Scoralite quality).

From FIG. 8 it can be seen that xylitol concentrations below or at 25% leads to tablets of fine compaction properties. The concentration of xylitol up to 25% has no impact on crushing strength whereas a concentration of 40% leads to capping tablets at high main compression forces. The use of the xylitol/sorbitol mixture, which is also at a high concentration of sugar alcohol, is not compactable at all. This matter is further discussed in example 6.

Figure 9:
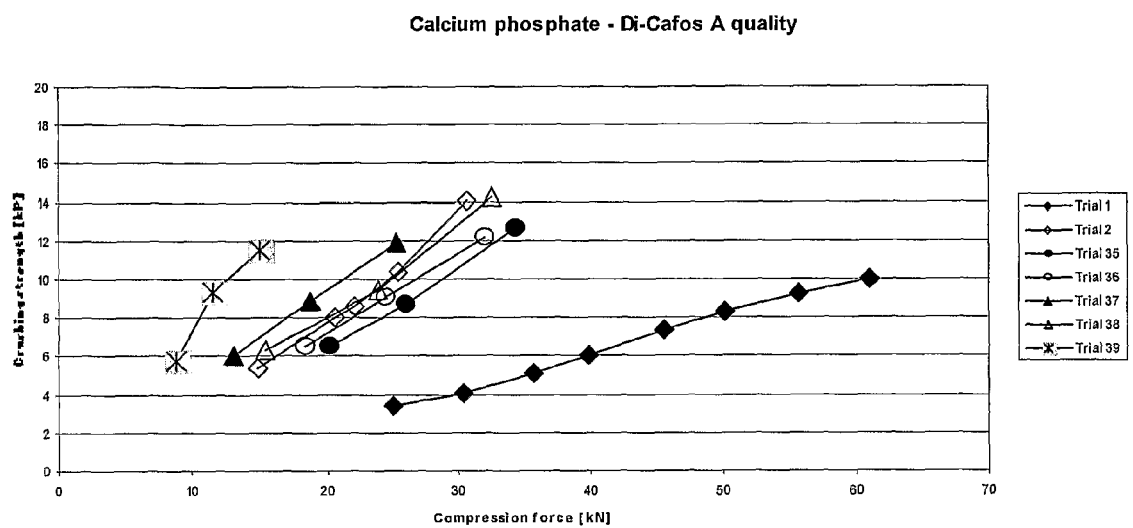
FIG. 9 is a line graph demonstrating the crushing strength of tablets based on polycristalic and porous dicalcium phosphate (Di-Cafos A quality) compared to crushing strength of tablets based on regularly shaped calcium carbonate (Scoralite quality).

From FIG. 9 can be seen all the used concentration of xylitol mixed with di-calcium phosphate in a Di-Cafos A quality leads to tablets comparable to tablets based on granulates where regularly shaped calcium carbonate and sorbitol with an optimal particle size are used (the inventors have previously found that sorbitol—that has a much smaller mean particle size than that of "instant sorbitol"—is much better to use when compacting it together with a regularly shaped calcium-containing compound). The mixture of xylitol/sorbitol has even better compaction properties. This matter is further discussed in example 6.

Based on this example, the inventors have surprisingly found that not all calcium phosphate qualities are equally easy to subject to roller compaction. The polycrystalline nature and the porosity have major impact on whether it is possible to roller compact calcium phosphate.

Example 4

Comparison of Tablets Based on Roller Compaction of Calcium Phosphate Containing Compounds with and without the Admixing of Sugar Alcohol The investigations were based on the following formulation:

TABLE 1

Formulation based on calcium phosphate. Trial numbers

|  | Xylitol amount (% w/w) |  | Xylitol/Sorbitol Amount (% w/w) |
| --- | --- | --- | --- |
|  | 0 | 5 | 30/10 |
| Tri-Cafos P [tricalcium phosphate] $Ca_5(PO_4)_3OH$ Psd 6 μm *, Trial No. | 46 | 15 | 19 |

* Psd: mean particle size based on D(v; 0.5)

Tri-Cafos P, Trial 46, was roller compacted as is, using parameters in accordance with example 1. Lubrication and tableting was also done as in example 1. Trial 15 and 19 are described in example 3.

Figure 11:
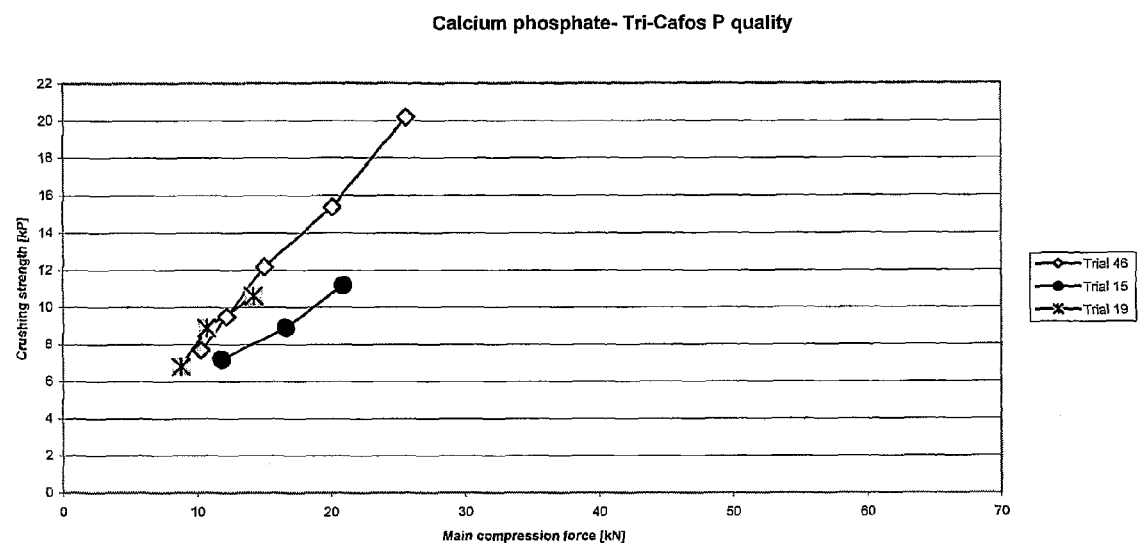
FIG. 11 is a line graph illustrating the crushing strength of tablets based on non-regularly shaped calcium phosphate (Tri-Cafos P quality) and xylitol (poor compaction properties) compared to tablets based on non-regularly shaped calcium phosphate (Tri-Cafos P quality) and mixture of xylitol/Sorbitol or without sugar alcohol excipients.
Figure 12:
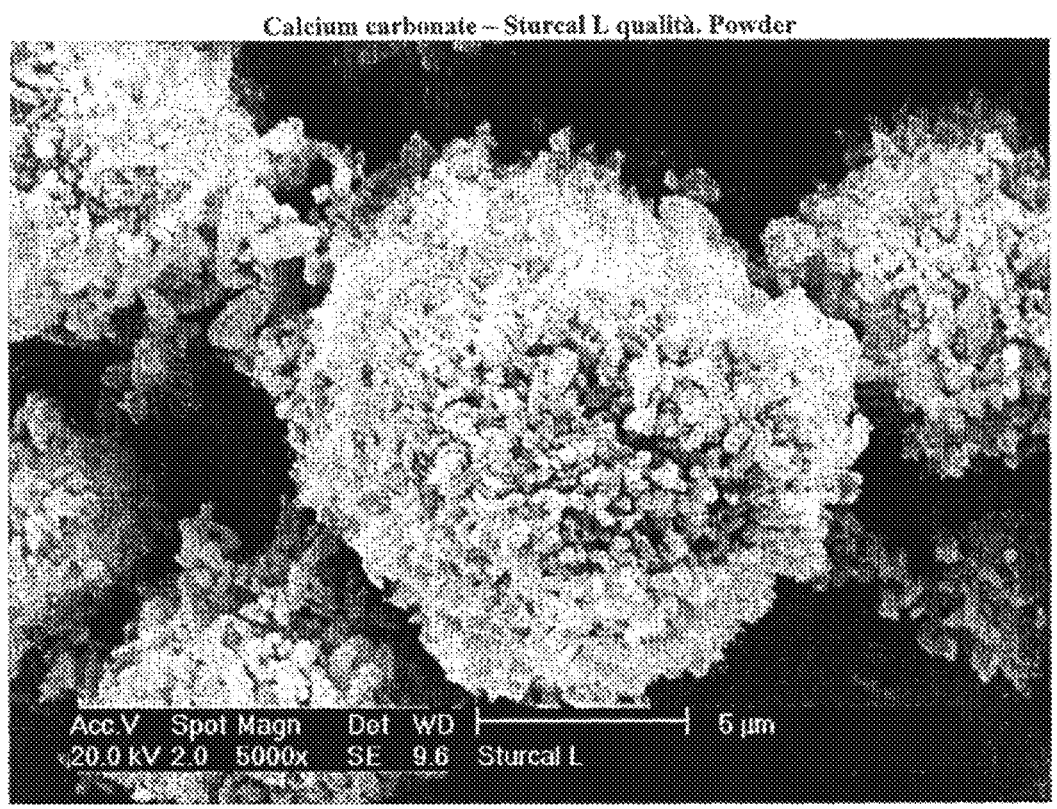
FIG. 12 is a photomicrograph illustrating scanning electron microscope (SEM)-Analysis of tablets based on non-regularly shaped calcium carbonate (Sturcal L quality).
Figure 13:
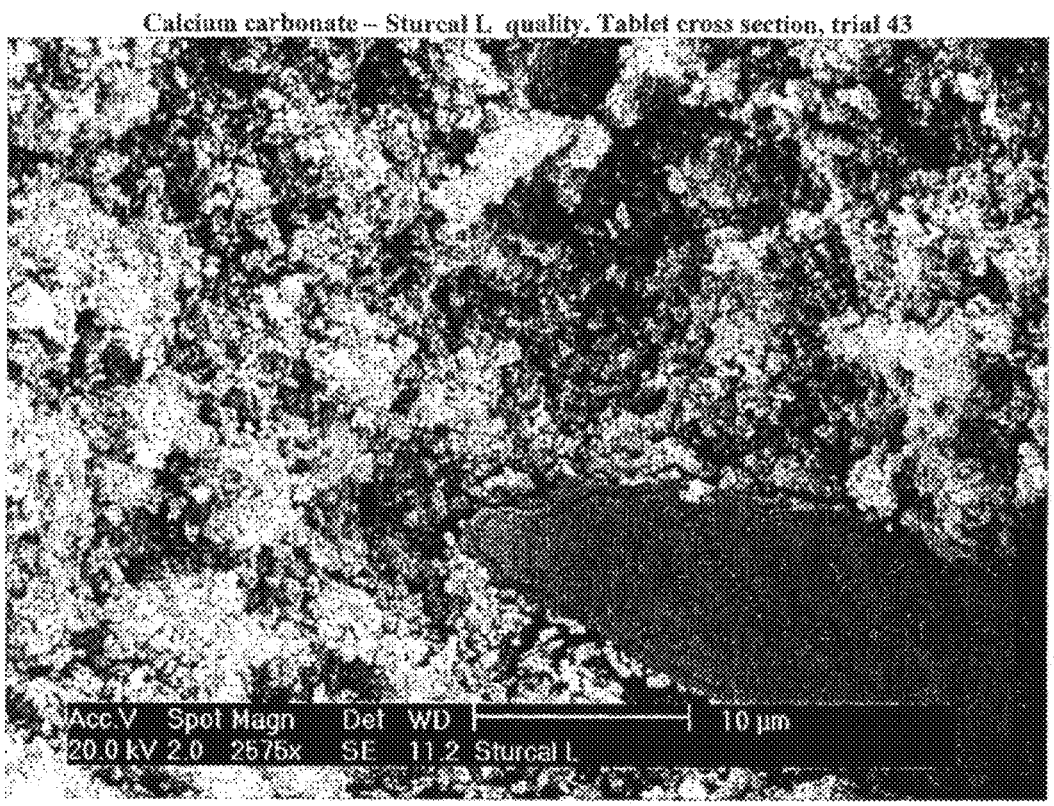
FIG. 13 is a photomicrograph illustrating SEM-Analysis of tablets based on non-regularly shaped calcium carbonate (Sturcal L quality); Tablet cross section.
Figure 14:
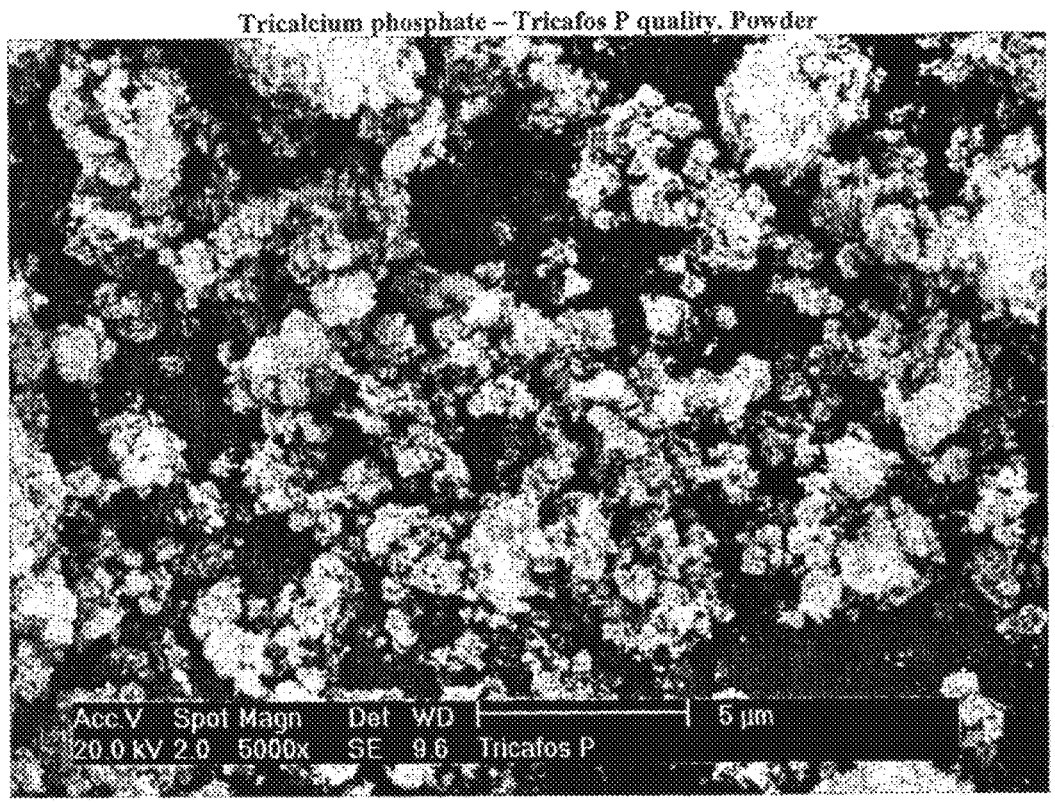
FIG. 14 is a photomicrograph illustrating SEM-Analysis of tablets based on non-regularly shaped calcium phosphate (Tri-Cafos P quality).
Figure 15:
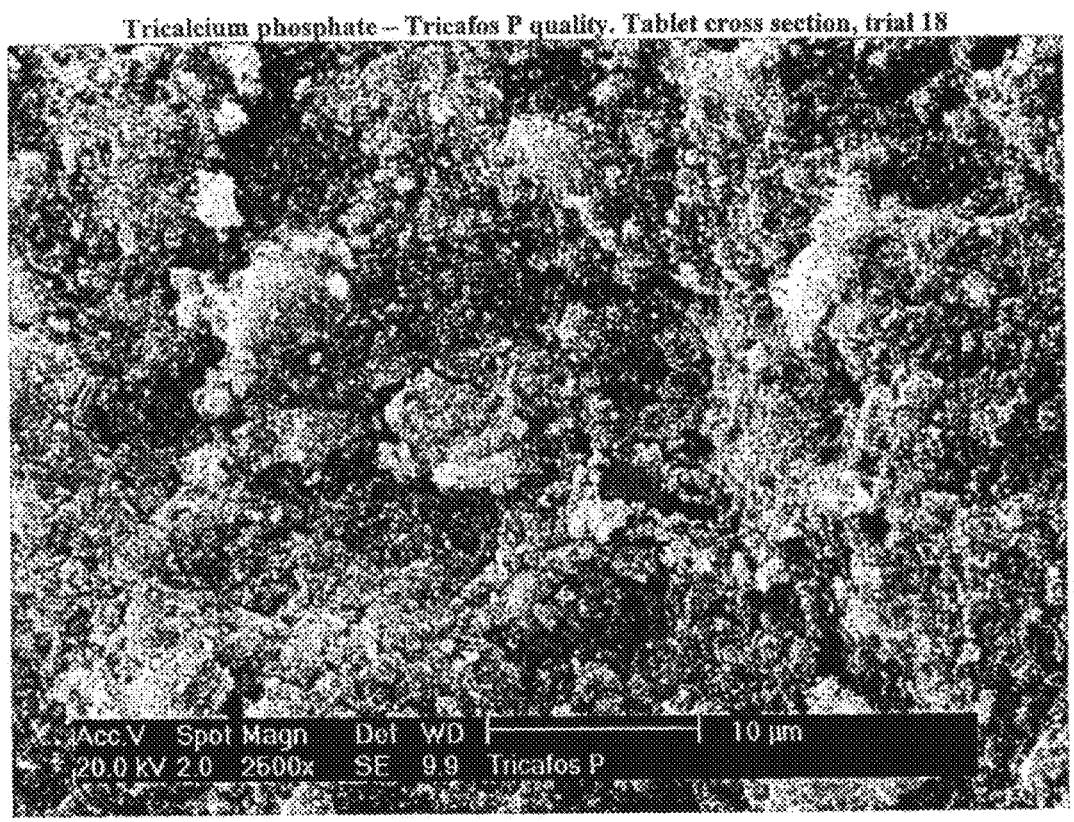
FIG. 15 is a photomicrograph illustrating SEM-Analysis of tablets based on non-regularly shaped calcium phosphate (Tri-Cafos P quality); Tablet cross section.

As seen in FIG. 11 the addition of an excipient with poor compaction properties, that is Xylitol as seen in FIG. 2 of example 1, results in tablets of poorer crushing strengths.

The addition to tri calcium phosphate of xylitol mixed with Sorbitol of the optimal particle results in crushings strengths similar what can be obtained with the pure tri calcium phosphate.

Example 5

Sensoric Evaluation of Tablets Based on Roller Compaction of Calcium Phosphate Compounds A sensoric evaluation was carried out on tablets from the following trials:
Trial 18 of example 3 containing tri calcium phosphate (Tri-Cafos P) and 40% xylitol Trial 35, 36 and 37 of example 3 containing di calcium phosphate (Di-Cafos A) and 5%, 10% and 25% xylitol respectively.

The sensoric test was carried out by 7 trained persons. Test was done according to ISO 8587 (ranking test) and ISO 5495 (paired test).

The result of this evaluation was the following:
For Di-Cafos A:
A content of 5% of xylitol is not optimal for taste masking
Variation of xylitol content between 10 and 25% has no significant impact on the taste masking properties of xylitol.
For all tablets tested the large particle size of the used Di-Cafos A resulted in a sand like sensation.
For Tri-Cafos P:
A level of 40% xylitol was required in order to obtain a similar taste masking as seen for Di-Cafos A.
Because of the small particle size a sand like sensation was not detected.

Example 6

Evaluation of Compaction Properties of Calcium Phosphate and Polycrystallic and Porous Calcium Carbonate Based on SEM-Analysis For powder qualities the following conclusions can be drawn:
Based on FIG. 12-15 it can be seen that a coherent tablet is obtainable if the calcium compound has a mean particle size around a few μm. Furthermore, each particle must be of a polycrystallic nature resulting in a porous structure. As seen in example 2, FIG. 10 and example 3, FIG. 5, the use of Sturcal L (calcium carbonate) or Tricafos P (tricalcium phosphate) leads to tablets of high crushing strengths.

Figure 18:
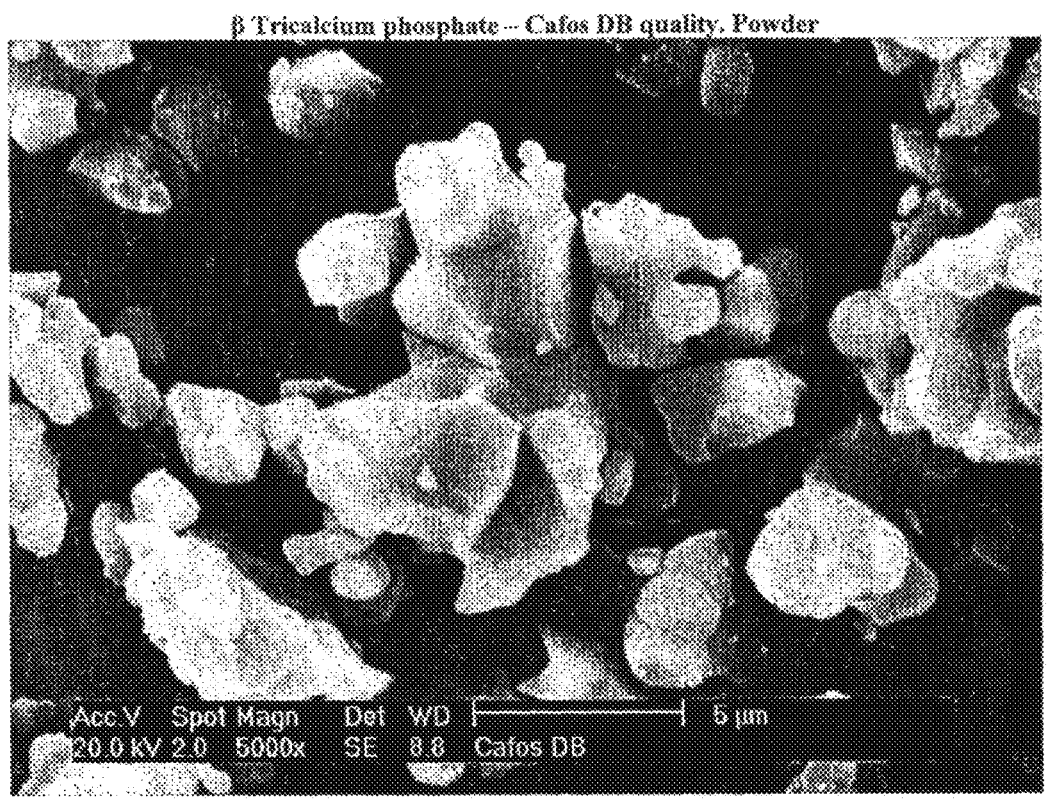
FIG. 18 is a photomicrograph illustrating SEM-Analysis of tablets based on non-porous tricalcium phosphate (Cafos DB quality).
Figure 19:
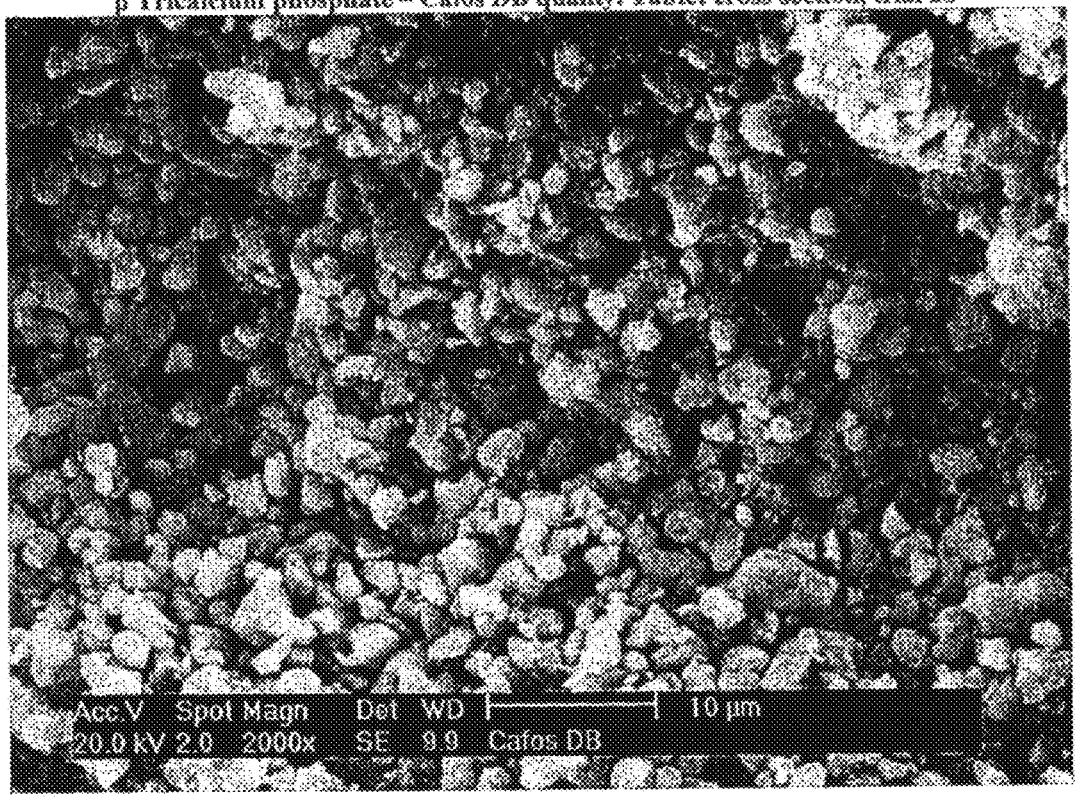
FIG. 19 is a photomicrograph illustrating SEM-Analysis of tablets based on non-porous tricalcium phosphate (Cafos DB quality); Tablet cross section.
Figure 23:
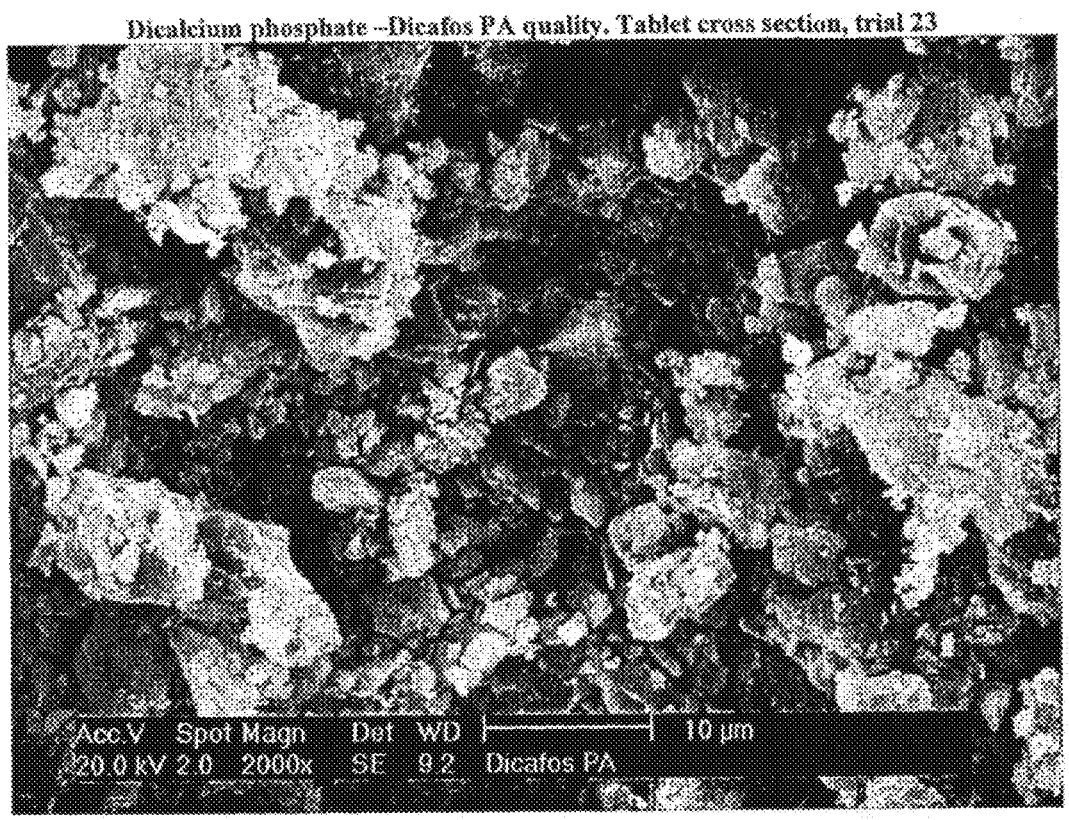
FIG. 23 SEM-Analysis of tablets based on non-regularly shaped calcium phosphate (Di-Cafos PA quality); Tablet cross section.

In contrast to this it can from FIGS. 18 and 19 be seen that particles of a non porous structure (Cafos DB, β-tricalcium phosphate) leads to non coherent tablets showing capping even at low compression forces. Furthermore, addition of sugar alcohol below 40% did not lead to satisfactory tablets as described in example 3. As the Dicafos PA (dicalcium phosphate) also is of a non porous structure (see FIG. 22 and FIG. 23) the same trend regarding crushing strength is seen. At the high concentration of xylitol the crushing strength is somewhat improved compared to Cafos DB as the capping tendency is less pronounced.

Figure 20:
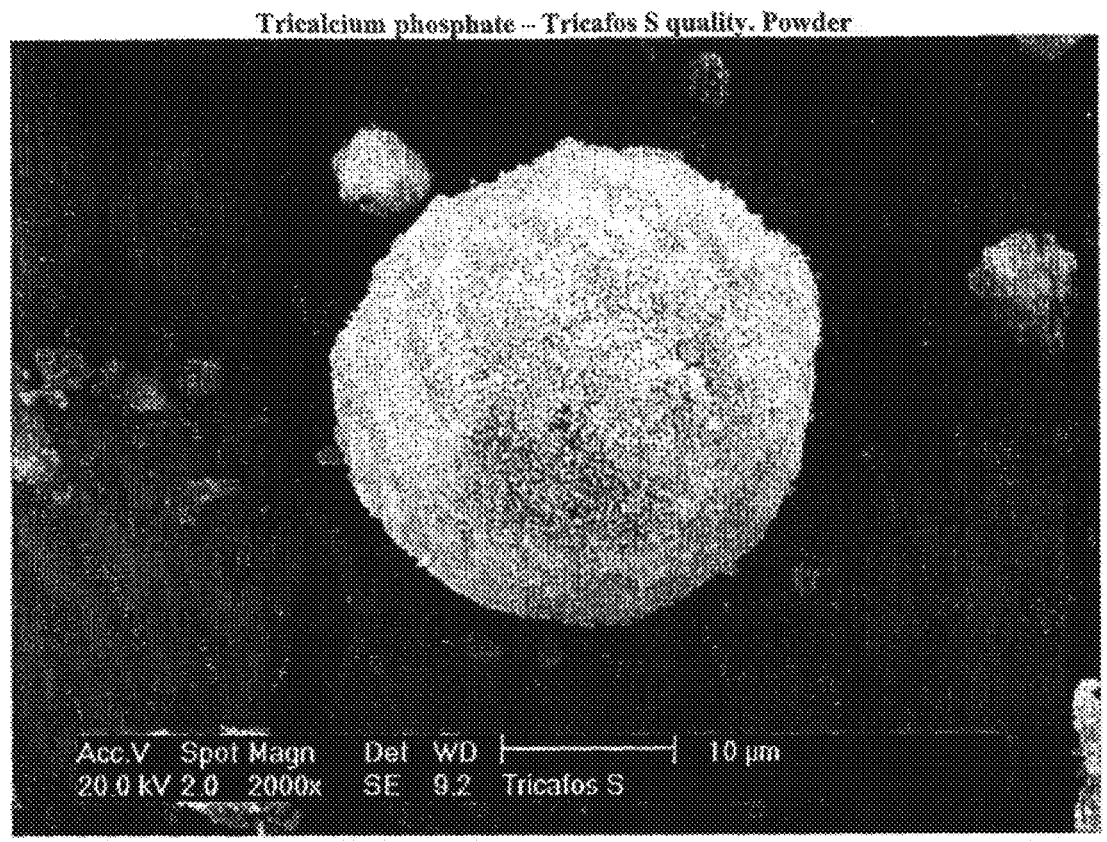
FIG. 20 is a photomicrograph illustrating SEM-Analysis of tablets based on non-porous tricalcium phosphate (Tri-Cafos S quality).
Figure 21:
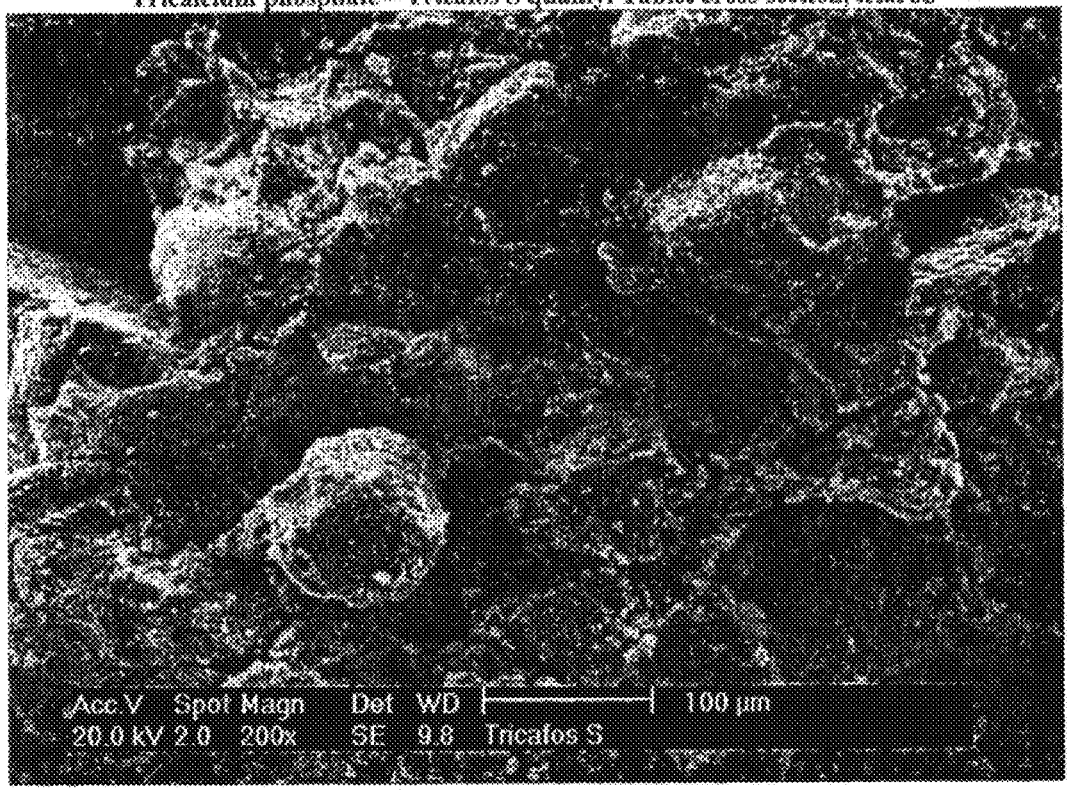
FIG. 21 is a photomicrograph illustrating SEM-Analysis of tablets based on non-porous tricalcium phosphate (Tri-Cafos S quality); Tablet cross section.

For direct compressible (dc) calcium qualities the following conclusions can be drawn:
From FIGS. 20 and 21 can be seen that if the calcium compound used is of a dc quality, even particles of a non porous structure as Tricafos S (tricalcium phosphate) will lead to tablets of high crushing strength, illustrated in example 3, FIG. 8. This is probably caused by particle fracture resulting in new surfaces ready for binding. However, a high concentration of xylitol counteracts this effect.

Figure 16:
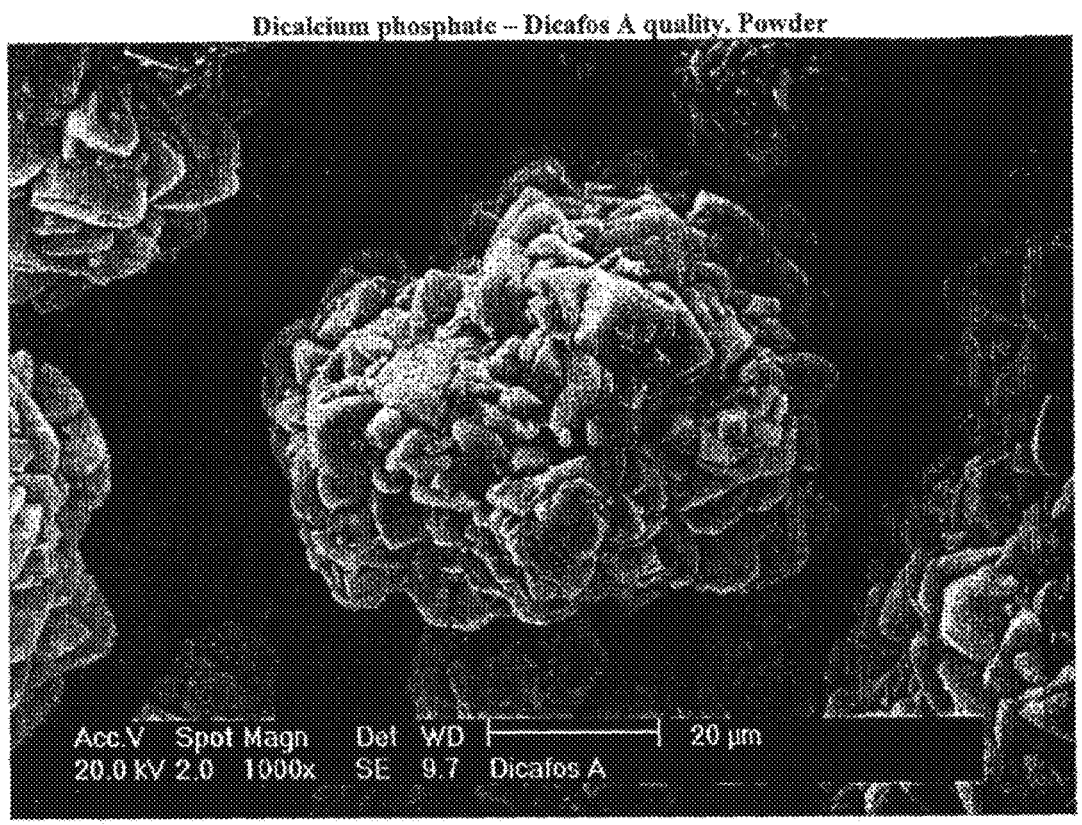
FIG. 16 is a photomicrograph illustrating SEM-Analysis of tablets based on polycrystalic and porous dicalcium phosphate (Di-Cafos A quality).
Figure 17:
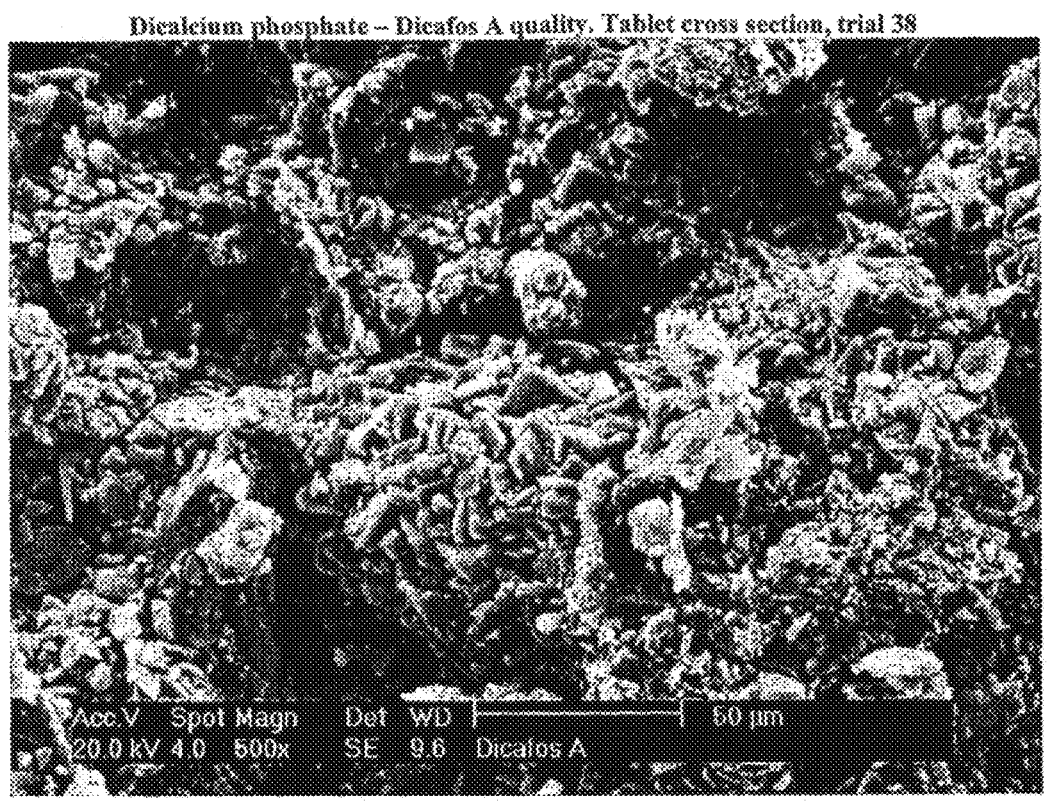
FIG. 17 is a photomicrograph illustrating SEM-Analysis of tablets based on polycrystalic and porous dicalcium phosphate (Di-Cafos A quality); Tablet cross section.

From FIGS. 16 and 17 combined with FIG. 9 in example 3, it can be seen that if the dc quality consist of particles having a poly crystallic nature resulting in porous structure as Dicafos A (dicalcium phosphate) the tablets will be of equal crushing strength as seen for porous particles having a size of a few μm as seen for Sturcal L and Tricafos P.

Based on this example it can be concluded that in order to obtain satisfactory tablet crushing strength when using a poor binder such as xylitol the following is required from the calcium compound:

For calcium carbonate:
Polycrystallic particles
The particles should have a porous structure
For calcium phosphate:
Particles having a mean particle size of a few microns
    The particles should be of a poly crystallic nature
    The particles should have a porous structure
Particles being of a DC-quality
    A porous structure of the particles is an advantage

The invention claimed is:

1. A method for the preparation of a pre-compacted material, the method comprising the steps of
   i) mixing one or more polycrystallic porous calcium-containing compounds with one or more sugar alcohols selected from the group consisting of xylitol, mannitol, maltitol, isomalt, and mixtures thereof, and
   ii) subjecting the thus obtained mixture to roller compaction,
   wherein the pre-compacted material prepared consists of one or more calcium-containing compounds and one or more sugar alcohols, the calcium-containing compound having a polycrystallic porous structure and the one or more sugar alcohols being selected from the group consisting of xylitol, mannitol, maltitol, isomalt, and mixtures thereof.

2. The method according to claim 1, wherein the concentration of the calcium-containing compound is about 60% w/w or more.

3. The method according to claim 1, wherein the concentration of the one or more sugar alcohols is about 5% w/w or more.

4. The method according to claim 1, wherein the calcium-containing compound is selected from the group consisting of calcium carbonate, calcium citrate, calcium lactate, calcium phosphate, tricalcium phosphate, dicalcium phosphate, calcium gluconate, bisglycino calcium, calcium citrate maleate, hydroxyapatite, solvates thereof, and mixtures thereof.

5. The method according to claim 1, wherein the calcium-containing compound is calcium carbonate.

6. The method according to claim 1, wherein the calcium-containing compound is in a direct compressible form.

7. The method according to claim 1, wherein the pre-compacted material prepared consists of precipitated calcium carbonate comprising scalenohedral calcite crystals and xylitol.

8. The method according to claim 1, wherein the pre-compacted material prepared consists of precipitated calcium carbonate comprising scalenohedral calcite crystals and mannitol.

9. The method according to claim 1, wherein the pre-compacted material prepared consists of precipitated calcium carbonate comprising scalenohedral calcite crystals and maltitol.

10. The method according to claim 1, wherein the total concentration of the one or more sugar alcohols is from about 5% w/w to about 40% w/w.

* * * * *